(12) United States Patent
Beck Arnon

(10) Patent No.: US 8,839,790 B2
(45) Date of Patent: Sep. 23, 2014

(54) NASAL INSERTS

(76) Inventor: Adva Beck Arnon, Giva'at Ada (IL)

(*) Notice: Subject to any disclaimer, the term of this patent is extended or adjusted under 35 U.S.C. 154(b) by 0 days.

(21) Appl. No.: 12/841,511

(22) Filed: Jul. 22, 2010

(65) Prior Publication Data

US 2011/0048430 A1   Mar. 3, 2011

Related U.S. Application Data

(60) Provisional application No. 61/229,449, filed on Jul. 29, 2009.

(51) Int. Cl.
*A24F 47/00* (2006.01)
*A61F 5/08* (2006.01)
*A61F 5/56* (2006.01)

(52) U.S. Cl.
CPC ... *A61F 5/56* (2013.01); *A61F 5/08* (2013.01); *A24F 47/00* (2013.01)
USPC ...................................... 128/207.11; 131/270

(58) Field of Classification Search
USPC .................. 128/858, 206.11, 207.18, 201.18, 128/205.27, 205.29; 604/2, 904; 424/400; 137/512.15; 606/162, 196; 131/270–271
See application file for complete search history.

(56) References Cited

U.S. PATENT DOCUMENTS

| | | |
|---|---|---|
| 2,274,997 A | 3/1942 | Thurman |
| 2,924,217 A | 2/1960 | Regel et al. |
| 3,145,711 A | 8/1964 | Beber |
| 3,463,149 A | 8/1969 | Albu |
| 4,267,831 A | 5/1981 | Aguilar |
| 4,573,461 A | 3/1986 | Lake |
| 4,887,597 A | 12/1989 | Holland |
| 4,984,302 A | 1/1991 | Lincoln |
| 5,117,820 A | 6/1992 | Robitaille |
| 5,395,309 A * | 3/1995 | Tanaka et al. .................... 604/18 |
| 5,568,808 A | 10/1996 | Rimkus |
| 5,601,594 A | 2/1997 | Best |
| 5,947,119 A | 9/1999 | Reznick |
| 6,004,342 A | 12/1999 | Filis |
| 6,015,425 A | 1/2000 | Altadonna, Jr. |
| 6,216,694 B1 | 4/2001 | Chen |
| 6,484,725 B1 | 11/2002 | Chi |
| 6,561,188 B1 * | 5/2003 | Ellis ......................... 128/206.11 |
| 6,971,387 B2 | 12/2005 | Michaels |
| 6,981,502 B2 | 1/2006 | McCormick et al. |
| 7,108,198 B2 | 9/2006 | Altadonna, Jr. |
| 7,156,098 B2 | 1/2007 | Dolezal et al. |
| 7,156,099 B1 | 1/2007 | Jenkins |
| 7,294,138 B2 * | 11/2007 | Shippert ....................... 606/196 |
| 2002/0153007 A1 | 10/2002 | Davi |
| 2002/0177871 A1 | 11/2002 | Santin |
| 2003/0094178 A1 | 5/2003 | McAuley et al. |

(Continued)

*Primary Examiner* — Patricia Bianco
*Assistant Examiner* — Camtu Nguyen
(74) *Attorney, Agent, or Firm* — The Webb Law Firm

(57) ABSTRACT

Methods of use of a nasal insert to support smoking cessation, and methods of use of a nasal insert to reduce or eliminate snoring, and a method of use of a nasal insert to reduce the severity or to eliminate obstructive sleep apnea, and a method of use of a nasal insert to gain smoother, easier breathing through the nose. The nasal insert comprises a body having an inner surface which defines an air passageway surrounded by an outer surface of soft, flexible material. The nasal insert body can have a first portion and a second portion where the outer surface of said nasal insert body is configured to the nasal cavity.

41 Claims, 11 Drawing Sheets

(56) References Cited

U.S. PATENT DOCUMENTS

| | | | |
|---|---|---|---|
| 2003/0209145 A1* | 11/2003 | Soper | 95/273 |
| 2005/0037031 A1* | 2/2005 | Jackson | 424/400 |
| 2005/0211254 A1 | 9/2005 | Olson | |
| 2005/0279351 A1* | 12/2005 | Lewis et al. | 128/200.23 |
| 2006/0272640 A1 | 12/2006 | Abullon | |
| 2006/0292254 A1 | 12/2006 | More | |
| 2007/0062538 A1* | 3/2007 | Foggia et al. | 128/207.18 |

* cited by examiner

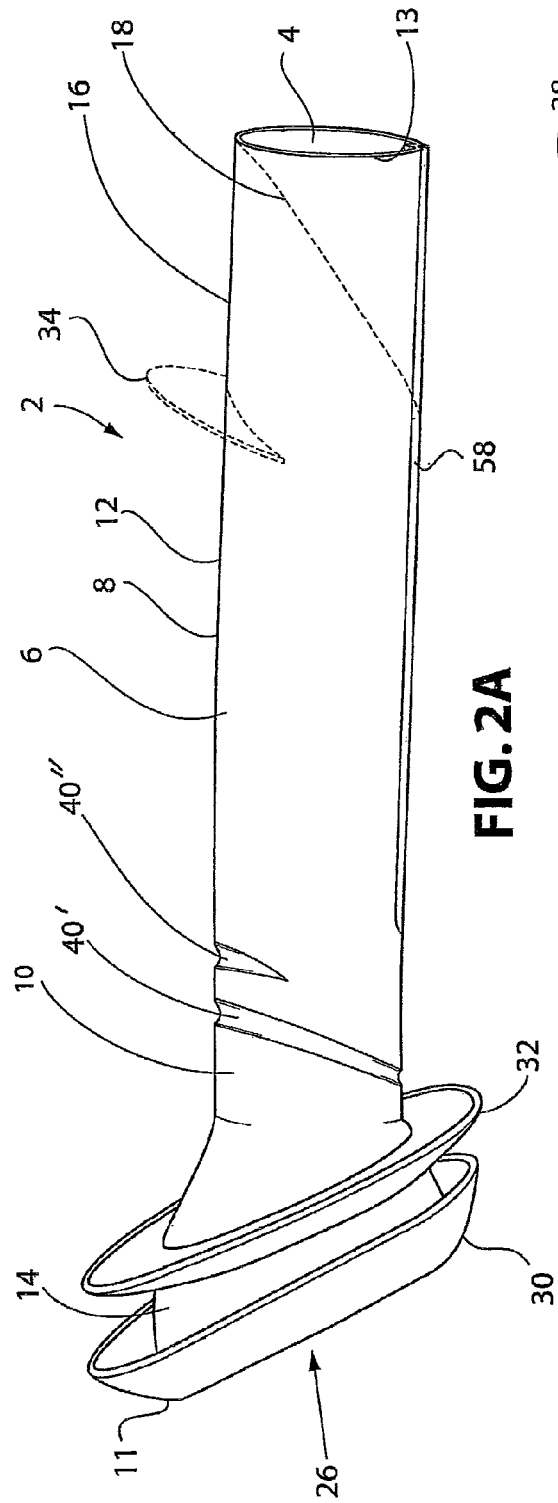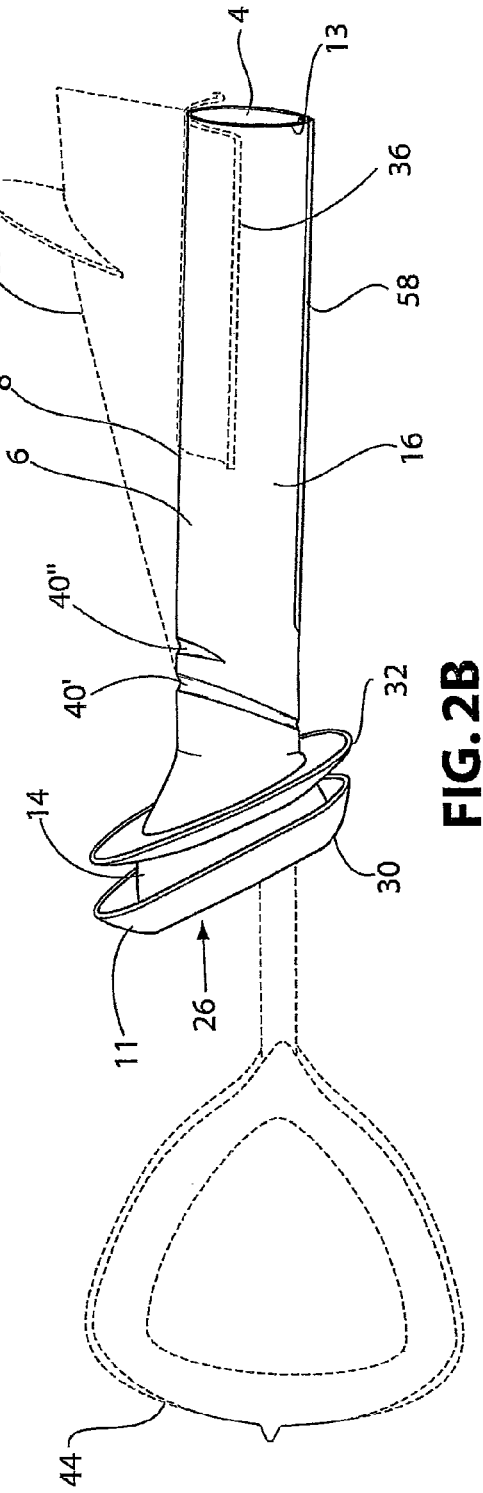

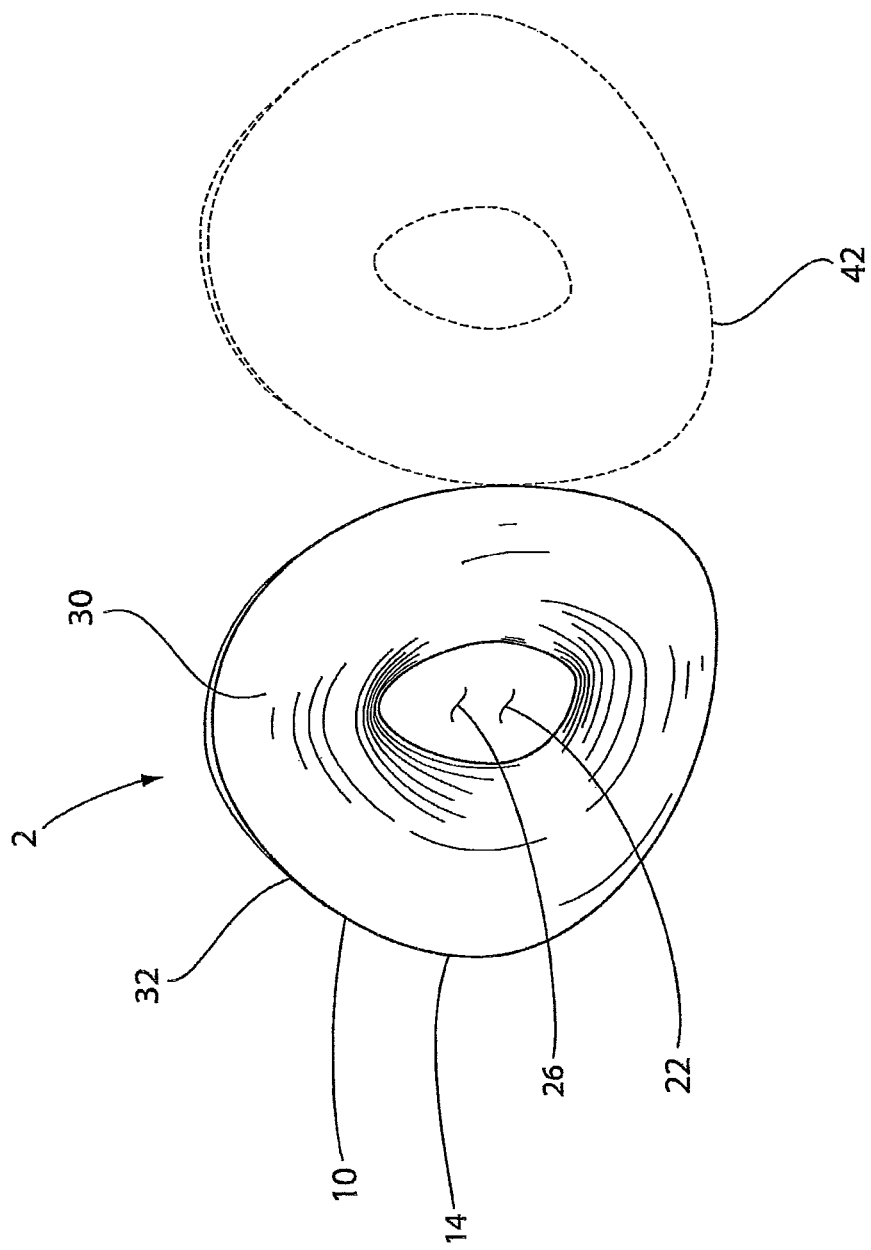

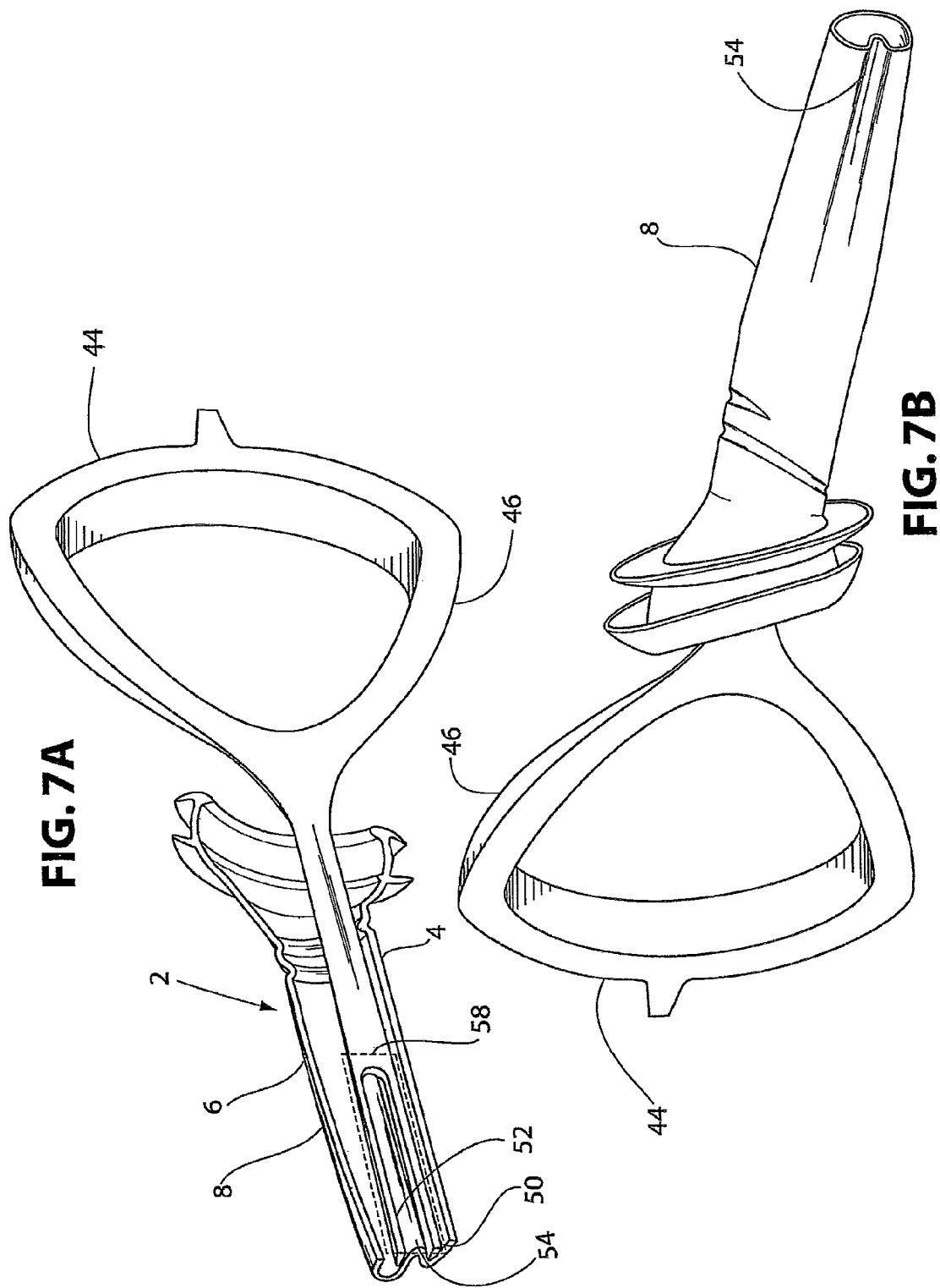

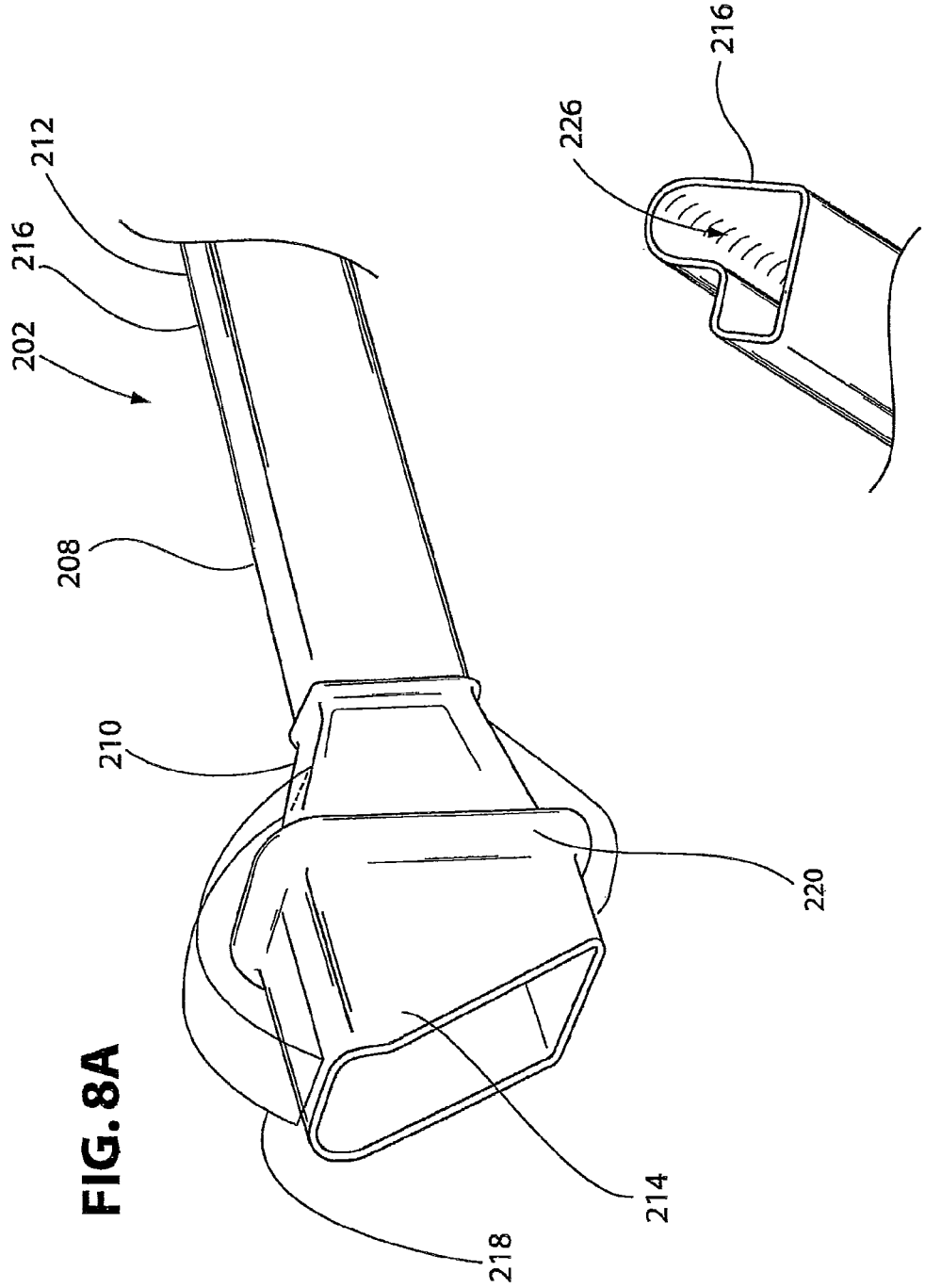

NASAL INSERTS

CROSS-REFERENCE TO RELATED APPLICATION

This application claims priority from U.S. Provisional Patent Application No. 61/229,449, entitled "Nostril Inserts", filed Jul. 29, 2009, which is incorporated herein by reference.

BACKGROUND OF THE INVENTION

1. Field of the Invention

The present invention relates generally to nasal inserts and, more particularly, to a method and apparatus for reducing or eliminating the urge to smoke by suppressing the body's physiological desire to smoke and by creating a less flavorful and enjoyable smoking experience. Smoking is among the most common health concerns of the modem world. Persons who smoke are prone to many respiratory and cardiovascular diseases and cancer.

2. Description of Related Art

There exists many smoking suppression or cessation programs to aid in reducing or eliminating the urge to smoke, such as nicotine replacement therapies, hypnosis, acupuncture, and self-help books. In addition, abrupt cessation of all nicotine use and various anti-depressant medicines have also proven to be viable means of smoking cessation.

Smoking a combustible smoking substance, such as tobacco or other tobacco-like substance, has been long recognized as an effective way to introduce drugs and substances into the user's bloodstream shortly after inhalation. The inhaled substances stimulate the olfactory region in the nasal cavity. Additionally, the inhaled substances trigger a physiological response in the brain due to there being similar to naturally-occurring substances commonly associated with the sensation of pleasure. This pleasure is in many cases due to satisfying the addiction to nicotine or to some other drug. Inhaling smoke produced by a combustible smoking substance has an adverse effect on one's health. The burning of the smoking material produces combustion byproducts and other particulate matter that is harmful to human health. Due to the addictive nature of the chemicals present in the smoke, smoking is an addictive habit that presents substantial challenges to smokers who desire to reduce or suppress their smoking habit.

It is known that taste and odor are physiologically interdependent, and distinct flavors are produced by aromas stimulating olfactory chemo receptors in the olfactory region of the nasal cavity. Complex flavors like ones associated with tobacco or tobacco-like substances, and others, can only be elaborated by smelling odorous particles from the vaporized gas and having the odorous particles come in contact with the olfactory region of the nasal cavity. Smelling is the sensation resulting from adequate stimulation of the olfactory organ. Therefore, smoking a cigarette, a cigar or any other smoking substance without being able to smell, or with a much weaker smell sensation, will be a tasteless and bland experience and, consequently, less enjoyable.

Another phenomenon commonly known by smokers is that it is very difficult to smoke during an illness, such as the flu, fever, runny nose etc. When a smoker attempts to smoke while being ill, he/she often feels sickness and disgust. As a result, many smokers smoke less while they are ill, or they eliminate all smoking during the length of the illness.

In addition, smoking is often related to daily actions and habits. For example, some individuals may be compelled to smoke every time they drink coffee. Impulse/automatic/conditioned smoking can be avoided or significantly reduced by neutralizing or preventing the odor of cigarette smoke from reaching the olfactory region. Even weakening the odor effect can reduce the impulse to smoke. Often, the perception of other smells that individuals associate with smoking may trigger the urge to smoke. Examples of such smells include the smell of coffee, barbeque, or the smell of other people's smoke. Having a weaker smelling sensation assists a person to overcome these moments and helps in avoiding the strong urge to smoke while confronting them.

Another cause of smoking is the enjoyment of the flavor associated with smoking a cigarette, cigar or other smoking substance. Since the odor of the smoking substance is one of the primary vehicles for heightening the smoking experience, many flavors such as mint or menthol are mainly sensed through smelling. Therefore, neutralizing the sense of smell, or even reducing it, while a person is smoking or is surrounded by other smokers, flattens the smoking experience and dramatically reduces the pleasure of smoking.

It is known that the first few days after an individual quits smoking are the most difficult barriers to overcome during the smoking cessation process. During the period when nicotine is expunged from the smoker's blood system, and the first few weeks afterwards, the smoker may experience strong urges to smoke. The urge to smoke also arises from the fact that smoking is strongly attached to daily routines and habits. For example, any break at work is a "cigarette break". Similarly, many smokers consider having a cigarette after lunch as the dessert.

Accordingly, there is a need in the art to provide a smoking cessation tool which reduces or eliminates the link between the smoker and the enjoyment of, or urge to smoke.

SUMMARY OF THE INVENTION

A method for reducing or eliminating smoking is based on using a nasal insert for supporting the user's smoking cessation efforts. The nasal insert may be an odor-preventing nasal insert for insertion into a nasal cavity that can prevent odors from reaching the olfactory region, or significantly reduce the intensity of these odors. The nasal insert does not necessarily have to be an odor-preventing insert. The nasal insert comprises a body having an inner surface which defines an air passageway. The nasal insert body can have a first portion and a second portion where the outer surface of the nasal insert body is suitable for insertion into the nasal cavity and may form a seal between the nasal insert body and the nasal cavity. The nasal insert body can rest against a portion of the nasal cavity. According to part of the embodiments, the nasal insert body can be configured to be fully inserted into the nasal cavity.

The present invention includes a method for reducing or eliminating smoking and the urge to smoke by suppressing the body's physiological desire to smoke and by creating a flat, flavorless and less enjoyable smoking experience. The steps of the method include providing a pair of odor preventing nasal insert bodies for inserting into the nasal cavities, wherein each of the nasal insert bodies comprises an inner surface defining an air passageway and an outer surface having a first portion and a second portion where the outer surface is adapted to form a seal between the nasal insert body and the nasal cavity. The user can insert the nasal insert bodies into the nasal cavities such that the nasal insert bodies fully and/or partially rest against a portion of the nasal cavities. Upon insertion, the seal is created between the nasal insert body and the nasal cavity. When the user breathes, the nasal insert body allows air only through the air passageway of the nasal insert body, thereby creating a bypass of the olfactory region and/or directing the air to bypass the olfactory region. This results in a flat and flavorless smoking experience that will contribute to reduction of smoking. In addition, the method may include providing a nasal insert for insertion into the nasal cavity, inserting the nasal insert into the nasal cavity, creating a partial or full blockage of the nasal cavity with or without creating the sealing discussed above, and contributing to the experience of symptoms similar to a mild cold. A nasal insert can be inserted into each nasal cavity, or it may be inserted into one nasal cavity only. In addition, the nasal insert body may or may not include an air passageway. Furthermore, inserting the nasal insert into the nasal cavity increases, for a period of time, the secretion of nasal mucus and contributes to a sensation of a light runny nose and mild cold symptoms. Thus, smoking while wearing the nasal insert results, for many people, in a feeling of sickness and/or disgust, and may also result in a flat and flavorless smoking experience. Consequently, smokers will totally avoid smoking or significantly reduce the amount smoked while wearing the nasal insert. In addition, the use of the nasal insert, when not used as an odor preventing nasal insert, will also create full or partial blockage of the nasal cavity and will cause a sensation of a mild cold and/or increase the secretion of mucus in the nasal cavity causing the sensation of a light runny nose.

Furthermore, by wearing the nasal insert, the odors from the outside environment or from inside the mouth opening can be entirely prevented from reaching the olfactory region of the user. Alternatively, a significant reduction in the intensity of odors reaching the olfactory region of the user can occur. The present invention thereby flattens the smoking substance flavor, flattens the smoking experience in general and reduces or eliminates the urge to smoke, which can be aroused by odors. Due to the reduced amount of odor stimulating the user's olfactory organ, the user will also not perceive the flavor of the smoking substance. As a result of the reduction in the flavor of the smoking substance, the user becomes less inclined to desire smoking and the smoking experience is less enjoyable. In some instances, the user's perception of the smoking substance flavor is completely eliminated. Another effect that the nasal insert may have is delaying the effect of odors to the olfactory region, causing a delayed smelling effect on the user which, in turn, will inhibit the user's interest in smoking. Additionally, the nasal insert can cause the sensation of a mild cold or light runny nose that causes the user to feel repulsion and/or sickness regarding smoking, and, therefore, causes the user to quit smoking or significantly reduce the amount of smoking while wearing the product.

Further, the method can include expanding the nasal insert body to fit within the nasal cavity. The expansion can be implemented by applying liquid to a nasal insert body, such as by using an applicator or by any other method. The nasal insert body, or part of it, rests within the inferior meatus of the nasal cavity or the middle and/or superior meatus of the nasal cavity. The nasal insert body can be used to provide drugs or medicine delivery to the user. The drugs may be aids for a smoking cessation process. The nasal insert body or part of it may further rest within the nasal vestibule of the nasal cavity. The nasal insert body can be used for anti-pollution or air purification to the respiratory system of the user. The method further can include using the nasal insert body to increase mucus secretion, which can then block, prevent, reduce or delay odors from reaching the olfactory region of the user and can also simulate a feeling of a mild cold or light runny nose, which for many people contribute to an automatic reaction of sickness and/or disgust while trying to smoke.

Furthermore, the invention includes a method for reducing or eliminating smoking and the urge to smoke by suppressing the body's physiological desire to smoke by using a nasal insert that is not necessarily an odor preventing one. Additionally, the present invention includes a method for reducing or eliminating smoking by providing a nasal insert that does not form a seal, or forms a partial seal, with the nasal cavity. Furthermore, the nasal insert air passageway may be fully or partially filled with different materials and may also be fully or partially blocked. The nasal insert may be inserted into both nasal cavities or to one nasal cavity only. The nasal insert in all embodiments of the present invention contributes to a sensation of a mild cold or light runny nose for a period of time, which results in the user's feeling of disgust and/or sickness while attempting to smoke.

When inserting the nasal insert body, the nasal insert body can be compressed from its initial shape or can be compressed in advance and then expanded after it is inserted into the nasal cavity. The nasal insert body extends into and rests against a portion of the nasal cavity and prevents or reduces odor from reaching the olfactory region of the nasal cavity. Alternatively, the nasal insert body can delay odor from reaching the olfactory region of the nasal cavity. In a further alternate embodiment, the nasal insert body can completely block the odor from reaching the olfactory region in the nasal cavity. An air lock can be formed inside the nasal cavity by using the nasal insert body and forming a pocket of air therein. When inserted fully into the nasal cavity, the nasal insert body can be undetectable from view outside the nose. In an alternate embodiment, the nasal insert body can partially extend outside the user's nose. In a further alternate embodiment, the nasal insert body can be located outside the user's nasal cavity.

In different embodiments of the nasal insert body, the nasal insert body is either worn continuously for a period of time or can be placed in the nasal cavity and worn only when the user decides. Preferably, the nasal insert body is placed in the nasal cavity when the user wakes up and it is removed before the user goes to bed. In yet another embodiment of the present invention, the nasal insert body is worn outside the nasal cavity. The nasal insert body can be disposable and/or biodegradable as well. The nasal insert body can be inserted, compressed, expanded, or removed by the user or the applicator.

Furthermore, the method includes wearing the nasal insert for a period of time, for example twelve hours, and then taking it out for a period of time, for example three hours or other periods of time according to instructions, allowing the nose mucosa to recover, as well as for other reasons. After this period, the user will wear the nasal insert again for a period of time, remove it again for a period of time, and so on. In addition, in case of use of a re-usable nasal insert, the method also includes washing or cleaning the nasal insert prior to re-using it. In the case of a disposable nasal insert, the user may insert a new nasal insert for each use. The method may also include using the nasal insert continuously, using the nasal insert only for selected periods of time, such as, for example, when the user is expecting to confront a temptation to smoke or specifically would like to avoid or reduce smoking for a period of time, or in any different manner that can support the target of use.

In addition to all the above, the nasal insert of this invention can be used for reducing and preventing snoring. The nasal area of the respiratory mucosa is particularly sensitive to changes in the blood flow and, when congested, it produces a partial or total blockage in the air passages. When a person is in a supine position, for example, when sleeping, the nasal congestion usually produces a partial blockage of the nasal airway. To overcome this blockage, an increase of negative pressure is required to maintain nasal respiration. The increase of negative pressure in the nose, together with muscle relaxation at sleep, will produce vibrations of the soft palate, which is the most common mechanism that causes snoring. By introducing the device into the nasal air passages, an open airway is achieved at the nasal level. Therefore, when used during sleep, the device will reduce or eliminate the snoring produced when sleeping in a supine position by maintaining open air passages at the nasal level. In this case, the method of use would be wearing the device in one nasal cavity, or in both nasal cavities, while sleeping and taking it out upon waking. In many cases, the use in one nasal cavity will be enough, but in order to achieve a stronger impact, the use in both nasal cavities would be preferred.

In addition, the nasal insert of this invention may be used for reducing and/or preventing obstructive sleep apnea. The same mechanism which increases negative pressure in order to maintain respiration when lying down, is responsible for the obstructive sleep apnea in most people suffering from this symptom. The obstructive sleep apnea is caused by collapse of the pharyngeal walls into the airway, which is produced by the combination of increased negative pressure in the air passages during respiration, while the person is in a supine position, and the relaxation of the pharyngeal muscles during sleep. The collapse of the pharyngeal walls will produce a partial or total blockage of air passages at the level of the oropharynx. By maintaining an open nasal passage, the device reduces the negative respiratory pressure, thus eliminating the main cause of air passage collapse at the pharyngeal level. The device, therefore, will reduce the severity or eliminate obstructive sleep apnea. Also, in this case, the method of use would be wearing the device in one nasal cavity, or in both nasal cavities, while sleeping and then taking it out upon waking. In many cases, the use in one nasal cavity will be enough, but in order to achieve stronger impact, the use in both nasal cavities would be preferred.

In addition to the above-described effects, the present invention may also have the effect of enlarging the nasal natural air passageway. The nasal valve is the narrowest air passageway of the upper respiratory system and it generates a large part of the overall natural nasal resistance to air flow. The nasal insert of this invention may force a larger cross section for air flow in the nasal valve area and contribute to easier breath in general, as well as to reduction or elimination of snoring or of obstructive sleep apnea. It may also assist athletes, students or any other person who needs increased air consumption and oxygen for a specific need, or in general.

These and other features and characteristics of the present invention, as well as the methods of operation and functions of the related elements of structures, and the combination of parts and economies of manufacture will become more apparent upon consideration of the following description with reference to the accompanying drawings, all of which form a part of this specification, wherein like reference numerals designate corresponding parts in the various figures.

BRIEF DESCRIPTION OF THE DRAWINGS

FIG. 2A is a side perspective view of a nasal insert made in accordance with the present invention;

FIG. 2B is a side perspective view of a nasal insert and applicator;

FIG. 3 is a front view of a nasal insert made in accordance with the present invention;

FIG. 7A is a cross section of another design of a nasal insert and applicator made in accordance with the present invention;

FIG. 7B is a side perspective view of a nasal insert and applicator made in accordance with the present invention;

FIG. 8A is a side perspective view of a nasal insert showing a rectangular-shaped nasal insert made in accordance with the present invention;

FIG. 8B is a rear perspective view of an L-shaped tail of the nasal insert of FIG. 8A made in accordance with the present invention;

DETAILED DESCRIPTION OF THE PRESENT INVENTION

Figure 1:
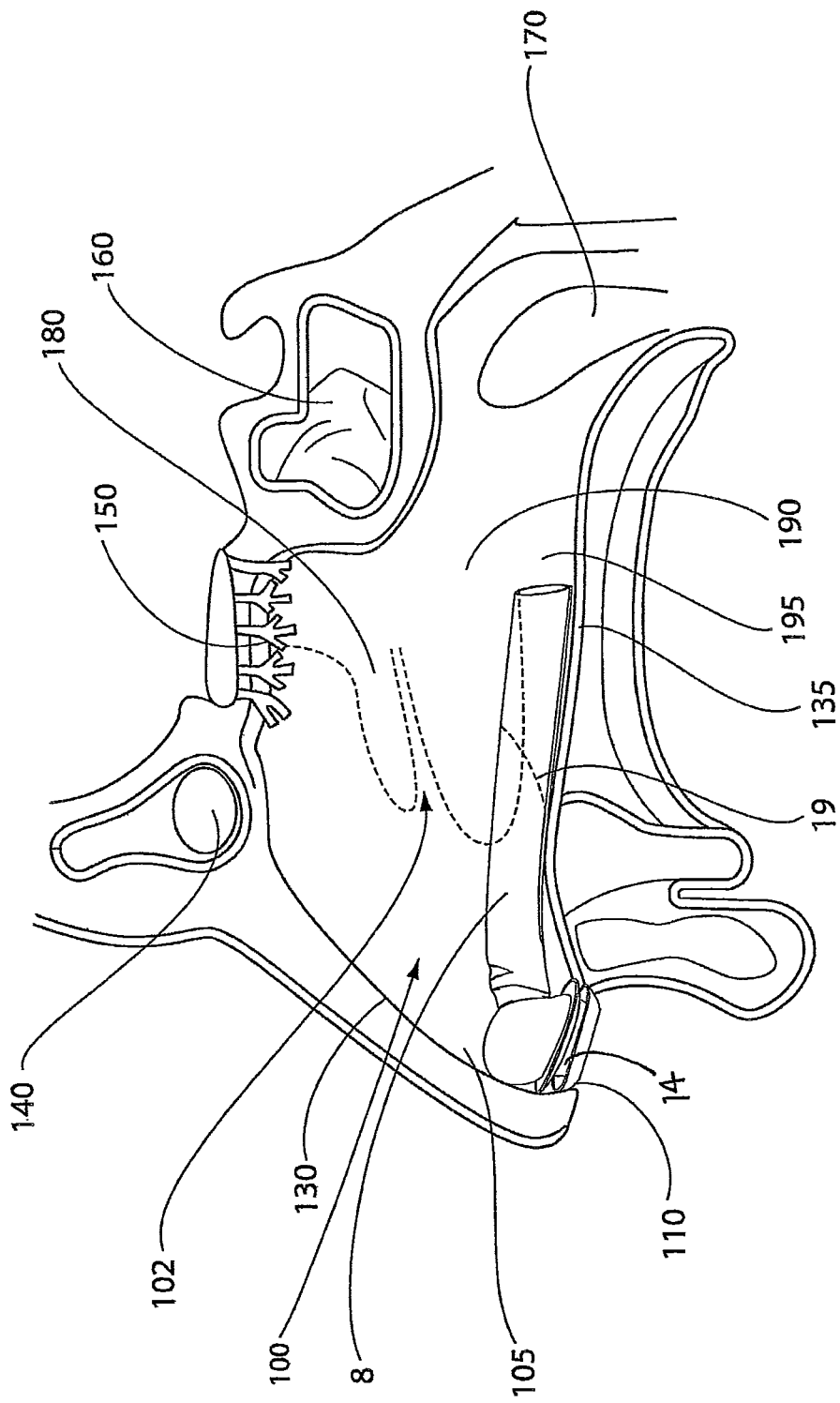
FIG. 1 is a cross section of a nasal passageway having a nasal insert made in accordance with the present invention.

For purposes of the description hereinafter, the terms "upper", "lower", "right", "left", "vertical", "horizontal", "top", "bottom", "lateral", "longitudinal" and derivatives thereof, shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

Figure 4:
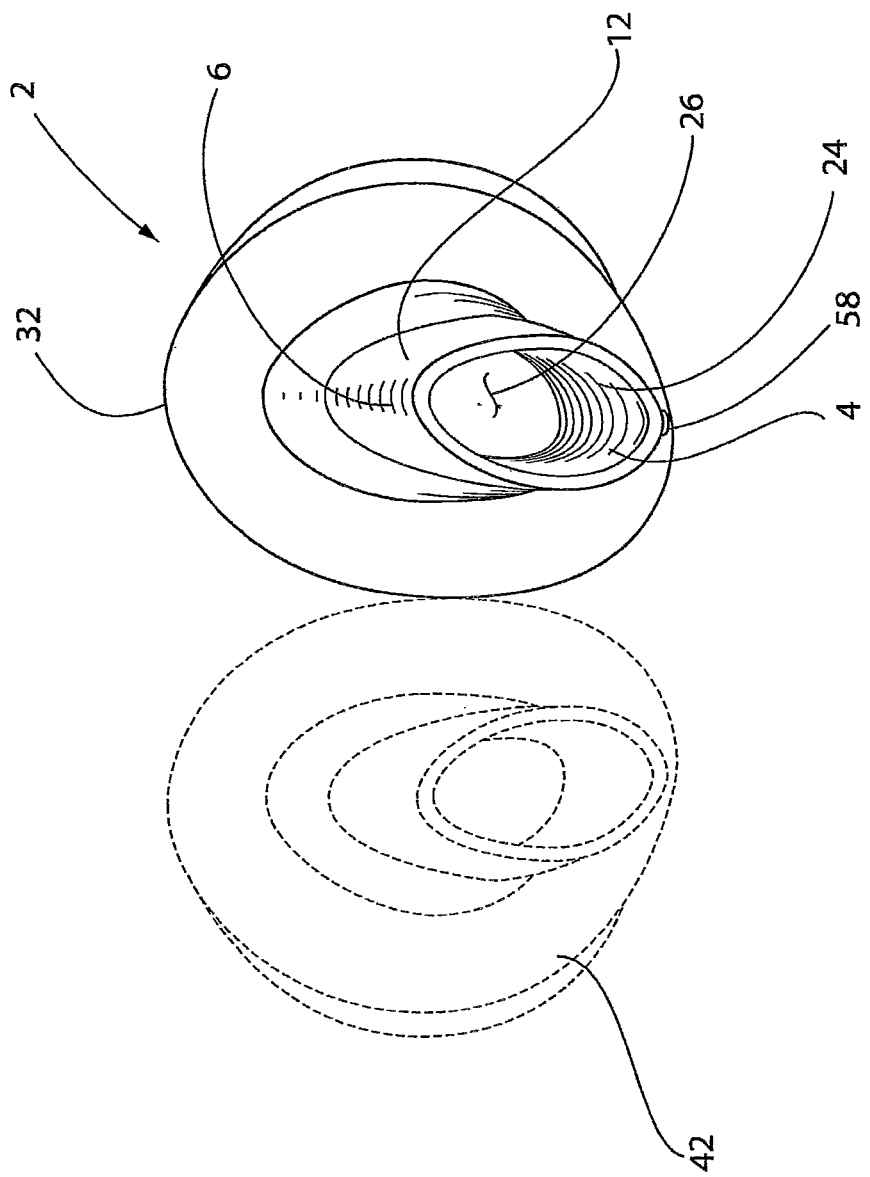
FIG. 4 is a rear view of a nasal insert made in accordance with the present invention.

With reference to FIGS. 2-4, a preferred embodiment of a nasal insert, generally indicated as 2, of the present invention is shown. Nasal insert 2 is used to prevent odor or to significantly reduce odor particles from reaching the olfactory region in the roof of the nasal cavity, thereby stopping or decreasing smells and flavors of smoke created by burning a smoking substance, such as tobacco or other tobacco-like substances. The nasal insert 2, includes a compressible body 8 having an inner surface 4 and an outer surface 6. The inner surface 4 of nasal insert body 8 defines an air passageway 26. The inner surface 4 forming air passageway 26 is rigid and yet flexible, enabling compression and expansion of air passageway 26, while always remembering and aspiring to return to its original shape to maintain an open air passageway. In an alternative embodiment, the inner surface 4 may partially or fully extend into the air passageway 26, such that the airflow through the air passageway 26 is partially or fully obstructed. The nasal insert body 8 will assume the shape of the nasal cavity, which may be different from its original shape, for example, outside of the nose the nasal insert body 8 may be oval, and while in the nose the nasal insert body 8 may be more bean-like or a smooth "L" shape. Also, because the nose conchas may be periodically expanding and shrinking as the user breathes, the nasal insert body 8 and, accordingly, the air passageway 26, are flexible enough to change their shape accordingly. Nasal insert body 8 will be rigid enough not to collapse and will maintain an open airway. The ability of the nasal insert body 8 to compress and expand also minimizes the pressure against the nasal mucosa, providing comfort. As shown in FIG. 3, with like numbers for like parts, the air passageway 26 begins at the upstream opening 22 and continuously extends through the nasal insert body 8 to the downstream opening 24, as shown in FIG. 4. Air passageway 26 extends throughout the entire length of the nasal insert body 8.

The nasal insert body 8 further includes a first portion 10 and a second portion 12. The first portion 10 includes an enlarged bulbous-shaped head 14. The shape of the head 14 is non-limiting, as other shapes can also be used, such as for example, a pear, oval, funnel, curved, straight, triangular, rectangular, or rounded head. The first portion 10 may be flexible to adapt to the specific shape of the nasal cavity. The second portion 12 extends from the first portion 10 to the end 13 of the nasal insert body 8 and is a substantially slightly curved cylinder having a substantially oval shape. In addition, the second portion can include a tapered tail. The second portion 12 may be flexible to adapt to the specific shape of the nasal cavity allowing a maximal cross section area for air passageway and minimizing pressure over the nasal internal mucosa through the periodical expansion and reduction of the conchas. The shape and size of the second portion 12 and of the tail are non-limiting and can vary as other shapes and sizes can be used having similar effects including round, bean, "L" shape, convex, straight, rectangular, curved, tapered, bulbous, or others. Further, the second portion 12 can also have a slanted tail 18 or a bulbous shaped tail 37 similar to the head 14 as shown in FIG. 2B, forming a large bulbous tail for gently leaning against the nasal septum of the nasal cavity 100.

When the nasal insert body 8 is inserted into the nasal cavity 100 as shown in FIG. 1, the nasal insert body 8 can be positioned inside the nasal vestibule 105 of the nasal cavity 100, so that the nasal insert body rests fully, and/or partially against a portion of the nasal cavities, forming a seal between the nasal insert body 8 and the nasal walls, and allowing air to pass through air passageway 26 while blocking air from passing around it. By moving through air passageway 26 the air is conducted to the posterior nasal cavity bypassing the olfactory area 150 located in the uppermost part of the nasal cavity. Nasal insert body 8 can also have a shortened tail 19 (shown in phantom), in which case air is still bypassing the olfactory region 150 because it is directed past. Thus, air passageway 26 of the nasal insert body 8 prevents air from reaching an olfactory region 150, either by bypassing the olfactory area 150 or by directing the air to bypass the olfactory area. The sense of smell originates in the nasal passageway. Odor particles stimulate the olfactory region 150 of the human nose. Nasal cavity 100, as shown in FIG. 1, includes a nostril 110, an upper nasal wall 130, a frontal sinus 140, and an olfactory region 150. The olfactory region 150 is covered by bipolar sensory neurons leaving the nose through the cribriform plate in the nasal roof synapsing in the olfactory bulb at the base of the frontal lobe of the brain. It is estimated that in the olfactory region 150, there are around six million sensory cells bilaterally. The olfactory senses reach the olfactory cortex in the rhinocephalon (not shown). Olfaction requires nasal air flow, which is part of respiration. The nasal cavities 100 further include nasal sinus 160 and nasopharynx 170. Also shown are the nasal conchas 180, 190. The inferior meatus 195 is located between the inferior concha 190 and the nasal floor 135. During normal respiration, most of inhaled air runs through the inferior and middle meatuses 195, 102 and only 10-15% of the inhaled air flows through the olfactory region 150 in the upper part of the nasal cavity 100, where odor is sensed. The specific route in which air goes into the nasal cavity 100 will determine which part of the air will come in contact with olfaction cells of the olfactory region 150. The air passageway 26 directs air to bypass the olfactory region 150 of the nasal cavity 100. By bypassing the olfactory region 150, odorous particulates are prevented from reaching that olfactory region and, by that, affecting a person's smoking experience, making it flat and unpleasant as well as reducing the urge to smoke.

To insert the nasal insert body 8 into the nasal cavity 100, the user can first compress the insert body 8 by squeezing it between the user's fingers. In addition, an applicator 44, shown in phantom in FIG. 2B and in cross section in FIG. 7A, can hold, squeeze and assist navigating the nasal insert body 8 and aid in preventing it from folding. The user can also just push the nasal insert body 8 into the nostril 110 and the nasal cavity 100 without compressing the nasal insert body at all.

Next, the user can then push the nasal insert body 8 into the nostril 110 and into the nasal cavity 100 to the inferior meatus, meaning between the inferior turbinate and the nasal floor, the second portion 12 being placed first inside the nostril 110. As shown in FIG. 1, when the first portion 10 is inside the nasal cavity 100, the bulbous head 14 is positioned to form a seal of the nasal vestibule inside the nasal cavity 100. A seal is produced between the head 14 and the nasal vestibule in the nasal cavity 100, forcing air to move in and out only through the air passageway 26 that bypasses the olfactory region 150 or directs the air to bypass the olfactory region 150. The seal that is formed in the nasal vestibule is not meant to be limiting as it may be formed in other locations at the nasal cavity, for example, at the nasal valve, and serve the same function. Also, the positioning at the inferior meatus is the preferred positioning, but other locations may be used, for example, the middle meatus. The seal formed between the head 14 and the nasal cavity, or elsewhere between the nasal insert body and the nasal cavity, also enables the formation of an air lock inside the nasal cavity 100. By forming an air lock inside the nasal cavity 100, stagnant air blocks new air from entering and, therefore, air is stopped or reduced from circulating inside the nasal cavity 100. Exhaled air from the rear of the nasal cavity is blocked or delayed from entering by the stagnant air remaining in the nasal cavity. Air circulation is stopped or significantly restricted when the air lock is formed. Thus, when an air lock is formed, it either prevents or significantly decreases odor from reaching the olfactory region 150. In addition, in case of a reduced, but yet existing circulation, the air lock delays the arrival of odor to the olfactory area.

In the preferred embodiment of the present invention, the user preferably inserts one nasal insert 2 into each nostril. In an alternative embodiment, the user may insert the nasal insert 2 into only one nostril. In such an alternative embodiment, the user benefits from the herein described advantages of the present invention, while retaining the full ability to smell. The nostril having a nasal insert 2 inserted therein will have, for a period of time, an increased secretion of nasal mucus as well as a partial blockage of the nostril, while the nostril without the nasal insert 2 will not. The user will, therefore, experience the symptoms commonly associated with a mild cold which, in turn, creates a feeling of sickness or disgust if the user attempts to smoke. Additionally, the user's ability to smell is not impaired because the user's other nostril is not obstructed.

In addition to the above-described effects, the present invention also has the effect of blocking part of the nasal cavity and also increasing the secretion of mucus in the nasal cavity. The presence of the nasal insert body 8 inside the nasal cavity 100 causes such a phenomenon, thereby making the user feel as if he/she has a mild cold. It has been found that many smokers who have mild cold symptoms (i.e., "a runny nose") are less inclined to smoke because of the decreased perception of the smell from the smoke and because smoking makes them feel sick and/or disgusted. The enjoyment of smoking is reduced or eliminated when smokers attempt to smoke while being ill. Smokers having a mild cold report the feeling of sickness or disgust when trying to smoke. By increasing the secretion of mucus in the nasal cavity, or by blocking part of the nasal cavity, the nasal insert body 8 creates a similar feeling of sickness or disgust that smokers experience when attempting to smoke while experiencing the symptoms of a mild cold. In simulating the symptoms of a mild cold, the present invention significantly reduces or entirely eliminates the user's impulse or general desire to smoke. The smoker remains healthy in all other respects and has no other symptoms of illness. In addition, the fact that the nasal insert is in the nasal cavity may create a situation where the respiration through the nose is a bit slower than usual. As a result, smokers who are inclined to exhale the smoke through their nose will experience discomfort in maintaining this practice. This discomfort associated with smoking, further aids in helping the smoker suppress or eliminate the urge to smoke and quit or significantly reduce smoking.

In addition to the above-described effects, the present invention also may have the effect of enlarging the nasal natural air passageway. The nasal valve is the narrowest air passageway of the upper respiratory system and it generates a large part of the overall natural nasal resistance to air flow. The nasal insert of this invention, in the relevant measure for such application, may force a larger cross section for air flow in the nasal valve area and contribute to easier breath in general as well as to reduction or elimination of snoring or of obstructive sleep apnea. In other words, the nasal insert passageway 26 cross section area or effective diameter over the complete passageway length is larger than the cross sectional area or effective diameter of the nasal valve when the nasal insert 2 is not placed within the nasal cavity. It may also assist athletes, students or any other person who needs increased air consumption and oxygen for a specific need, or in general.

The nasal insert body 8 can be formed of one or more materials, and is primarily a soft, flexible, and in some cases, spongy body 8. The outer surface 6 of the nasal insert body 8 can serve the important purposes of absorbing mucus and facilitating the run-off of mucus. In addition the outer surface 6, or part of it, can be used for forming a seal between the nasal cavity 100 and the nasal insert 2 and for sealing the nasal insert itself, or to support backward drainage of the mucus. In the first case, when the outer surface 6 is used to absorb mucus, materials that are primarily absorbent can be used to form the outer surface 6 or part of it. Absorbent materials that can be used include, for example, cotton, hydro-gels, Merocell®, polyethylene glycol, types of polyurethane or polyvinyl chloride, any type of suitable foam or any other suitable materials or combination of materials. The type of material is not meant to be limiting. A sealant material can also be used on the outer surface 6 of nasal insert 2 to seal the nasal insert 2. The sealant material can block odors and also facilitate mucus to run-off away from first end 11 toward a second end 13 of the nasal insert body 8 and into the nasal cavity 100. Materials suitable to form a strong seal can include silicon, Tygon®, any other plastic or combinations thereof, or any other suitable materials. In the case of forming a seal between the nasal cavity and the nasal insert, both absorbent or non-absorbent materials can be used, for example, cotton, hydro-gels, Merocell®, polyethylene glycol, silicon, any type of polyurethane, polyvinyl chloride, Tygon®, and other suitable materials. The outer surface 6 can be compressed or altered for smoother insertion, gaining a larger size after being placed in the nasal cavity. The inner surface 4, which forms the air passageway 26, can be made of a more rigid material that is also flexible and elastic in order to enable the air passageway 26 to expand and remember its original shape after it has been compressed or altered in some way. The material of the inner surface 4 may be selected to enable insertion of the insert without folding in cases when the applicator is not used. Examples of suitable materials include silicon, Tygon®, types of plastic or any combinations or suitable material. Between the inner surface 4 and the outer surface 6, any number of additional layers can be included to form nasal insert body 8. Each layer of nasal insert body 8 materials can include spongy material, sealant material, absorbent material, antibacterial material, alternative odor, anti-pollutions, or medicine, including but not limited to, hydro-gels, silicone, Tygon®, cotton, Merocell®, silicon, polyurethanes, polyvinylchloride, dimethylpolysiloxan, silicic acid, azodiacarbonamide, reticulated foam, polyethers, polyesters, polysiloxanes, polycarbonate, polyolefins, polybutyrates, polyethylene teraphtalate (PET), Polymides, polyethylene glycol, activated carbon, biodegradable material, anti-microbial agents, plastic materials, silver, bamboo, antimony, aluminum, metal materials, polymers, wood, resins, carbon based materials, carbon nanotubes (CNT), esters. The particular type of material used for the layers of the nasal insert body 8 is not meant to be limiting.

Alternatively, air passageway 26 can be filled or partially filled with a porous material to absorb odors, or for other uses, air can be allowed to pass through, and the porous material can trap or neutralize odorous particles. In yet another alternative of the preferred embodiment, the air passageway 26 can be filled with a material that completely or partially obstructs the airflow through the air passageway, thereby compelling the user to increasingly breathe through the mouth. The inner surface 4 and the outer surface 6, as well as any layer between them, can be partial layers or combinations of partial layers and full layers and/or full layers only or any other combination. On the other hand, they can all be made of the same material and/or be one layer, as long as the structure and material support the characteristics of softness, rigidity, flexibility, and others as defined above and hereinafter. In lieu of a passageway, the nasal insert can be made entirely of a porous material. In an embodiment where the air passageway is at least partially obstructed, respiration through the nose is less comfortable and slower than usual. As a result, smokers who are inclined to exhale the smoke through the nose while smoking will experience discomfort in maintaining this practice. Such discomfort associated with smoking further aids in helping the smoker suppress or eliminate the urge to smoke and to quit or significantly reduce smoking. The rigidity and the softness of the inner and outer surface can be the same.

In some embodiments the outer surface 6 can include a sealant material formed only on the head 14 of the first portion 10, the second portion can be made of absorbent material, with a sealing layer throughout the inner surface 4. The sealing layer of inner surface 4 can limit odor from penetrating the nasal insert body 8 and reaching the olfactory region 150, while the absorbent outer surface 6 reduces mucus and the sealant head 14 blocks air from flowing around the device and directs it. The sealing layer and the absorbent layer of the second portion can be the same layer and material. Alternatively, the nasal insert body 8 can be made of only one material, such as silicon, when the rigidity, softness, flexibility, resilience and other characteristics may be achieved by different thickness, stiffness, resilience, shape, grooves and other manageable parameters.

The nasal insert 2 can also be used to deliver odors. To deliver odor, the nasal insert body 8 can be made of natural materials or artificial materials, such as esters, which have inherent odor, or where odor can be added to the insert material. Alternatively, the materials of one or both of the inner and outer surfaces 4, 6 or any other layer of nasal insert body 8 can be impregnated with odorant particles or coated in order to deliver odor. For example, any surface of the nasal insert body 8 may be impregnated with any flavor commonly associated with tobacco or tobacco-like substances. Also, odor can be applied to the relevant element by an external tool such as an applicator.

In addition, the nasal insert 2 can provide medication. In such a case, medicine can be coated on one or both of the inner and outer surfaces 4, 6 or on another layer of the nasal insert 2, or can be applied to it through an external applicator. Alternatively, the materials of one or both of the inner and outer surfaces 4, 6 or any other layer of nasal insert body 8 can be impregnated with medicine or coated in order to deliver medicine. For example, one or both of the inner and outer surfaces 4 and 6, respectively, or any other layer of the nasal insert body 8 may be coated with a nicotine substance to help reduce the smoker's craving and urge to smoke or any other substance that may support smoking cessation. Also, antibacterial materials such as nanoscale silver or silver ion or bamboo or medicine can be used when making the composition of the nasal insert body 8, or coated thereon.

With reference to FIGS. 2A and 2B, nasal insert body 8 can include a flexible sealing member 30 in order to create a tight seal between the nasal insert body 8 and the nasal cavity 100. Sealing member 30 can be an outward extending leaf from head 14 of the first portion 10 of the nasal insert 2. The sealing member 30 can be a convex shaped leaf extending outward from the outer surface 6 of the head 14 of the first portion 10. The flexible yet rigid properties of sealing member 30 are adaptable to form a tight seal between the nasal insert body 8 and the nasal cavity 100 when the nasal insert body 8 is placed into the nasal cavity 100. The sealing member 30 may have spring characteristics and also is positionable to provide a corresponding match to the internal contour of the nasal cavity 100. The sealing member 30 can seal the nasal vestibule 105 and direct the inhaled air through the air passageway 26 of nasal insert 2. The sealing member 30 can provide an absolute seal and assure all nasally inhaled air will enter the air passageway 26 through the nasal insert 2. The sealing member 30 can also form an air lock after the nasal insert 2 is inserted into the nostril 110. The sealing member 30 can also be located in a different place on the nasal insert body and can have a different shape. The specific location and shape are not meant to be limiting as many can serve the purpose.

Multiple sealing members can be attached to the nasal insert body 8. As shown in FIGS. 2A and 2B, a second sealing member 32 can be placed on the head 14. The second sealing member 32 can be adjacent to the first sealing member 30, extending outward from the outer surface 6 of nasal insert body 8. The second sealing member 32 combines with the first sealing member 30 to create better sealing and to better form an air lock after the nasal insert 2 is placed in the nostril 110. A third sealing member 34 (shown in phantom) can extend from the outer surface 6 of the second portion 12. A fourth sealing member 36 (shown in phantom) can extend along the second portion 12 of the nasal insert body 8. Additionally, as shown in FIG. 2B, nasal insert body 8 can have a bulbous tail 37 (shown in phantom) having an optional sealing member 38 thereon or different sealing members. The number and placement of sealing members is not meant to be limiting, as different combinations can be combined to create a desired airflow to block or prevent or reduce or delay odor from reaching the olfactory region.

A sealing member can also be formed of layered material on the nasal insert body 8. For example, the head 14 can have sealing material attached on its surface to define a sealing member of material. The sealing material can be shaped to provide characteristics of the sealing members. On the other hand, it can be made with no additional layer or specific sealant member by suitable shape of the nasal insert body 8. In addition, any of the sealing members discussed can alternatively be partial sealing members as there is no requirement to completely surround the nasal insert body 8. The air lock can be formed in the upper nasal cavity.

Figure 5:
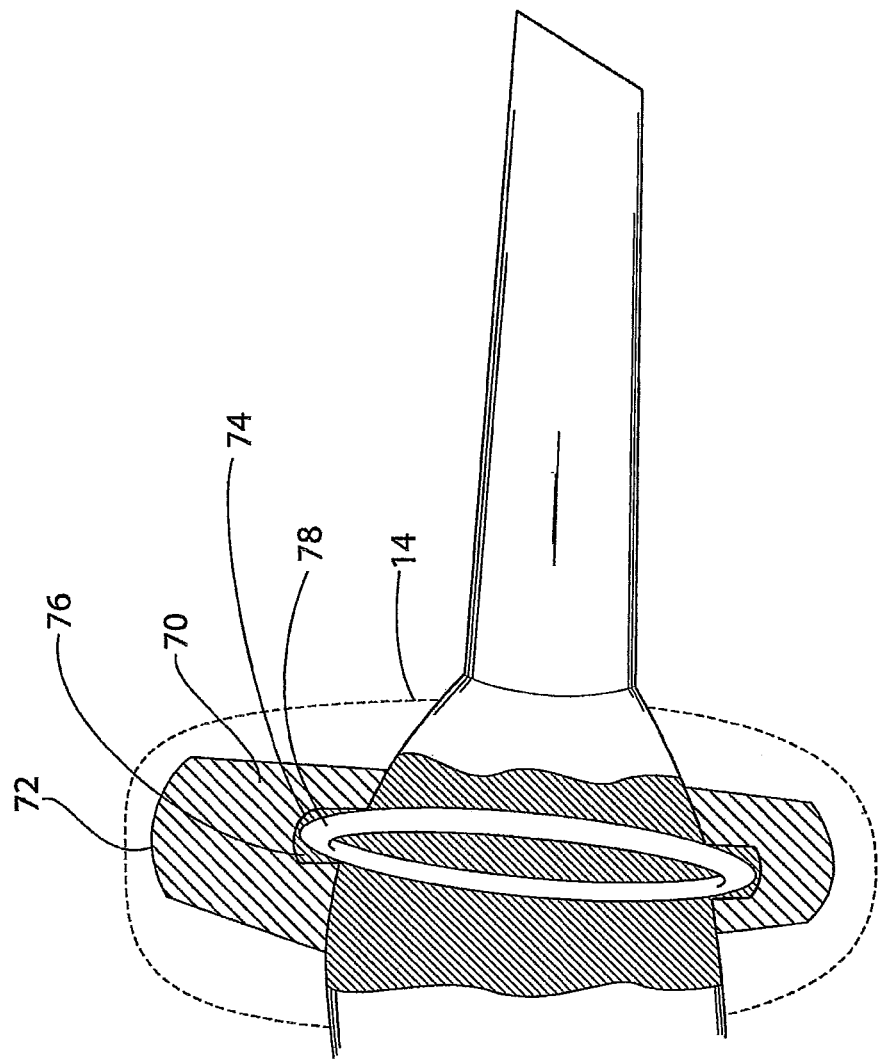
FIG. 5 is a side cross section of a nasal insert in accordance with the present invention.

With reference to FIG. 5, nasal insert body 8 is shown having an alternative sealing member 70. Sealing member 70 extends from head 14 and includes an inner surface 74 and an outer surface 72 forming a sealing member extending outward similarly to that of sealing member 30; however, an inner surface 74 of sealing member 70 forms a groove 76 that may receive a ring member 78, or may alternatively receive a spring member (not shown), or remain empty. When a ring member 78 is inserted in groove 76, the sealing member 70 is stretched and strengthened and can form a tight seal between the sealing member 70 and the nasal cavity 100. The ring member 78 can be replaced when it becomes loose or if the nasal insert body 8 is to be removed. The outer surface 72 can be made from a different material than the inner surface 74 or of the nasal insert head 14. The material can be absorbent or non-absorbent. The cavity formed by the inner surface 74 is also a grip, enabling the material of the outer surface 72 to be mechanically connected to the internal surface 74 and to the nasal insert head 14 or body 8 in general. The outer surface may fully or partially surround the head and may also form different shapes (shown in phantom). The method and materials of sealing, sealing members and their connectivity to the nasal insert portions is not meant to be limiting, as many different alternatives may be applied to perform the sealing. For example, instead of having a bulge as a grip, a niche, pin or some adhesive material can be used (not shown). Also, all of this mechanism can be located elsewhere on the nasal insert body 8.

Referring back to FIGS. 2A and 2B, a nasal insert body 8 may further include a flexible joint 40 defined by grooves 40' and 40" formed in the nasal insert body 8 and shown between the first portion 10 and second portion 12. The flexible joint 40 is formed by a groove or series of grooves defined through all or part of the layers comprising nasal insert body 8. The groove or series of grooves may be located between the first and second portions 10, 12 of the nasal insert body 8 or in other locations on the nasal insert body 8. The flexible joint 40 provides increased flexibility and can minimize the effect of movements of one nasal insert portion in regard to the other nasal insert portion to provide higher comfort. The increased flexibility can further minimize pressure against the nasal mucosa; the flexible joint 40 provides flexibility for the second portion 12 to bend with relation to first portion 10. Flexible joint 40 provides flexibility when navigating and inserting the nasal insert 2 into the nasal cavity 100. Still further, facial expressions which move the nose can be buffered in their effect on the nasal insert body 8 as the nasal insert 2 can flex at the flexible joint 40 to accommodate the movements. The flexible joint 40 is optional as embodiments with different joints or without high flexibility joints at all may serve as well.

FIG. 3 shows a right and left nasal insert 2, 42 (shown in phantom). When inserted into the nasal cavity, the nasal inserts 2, 42 can fit and be oriented for the left and right nasal cavities, respectively.

Figure 6A:
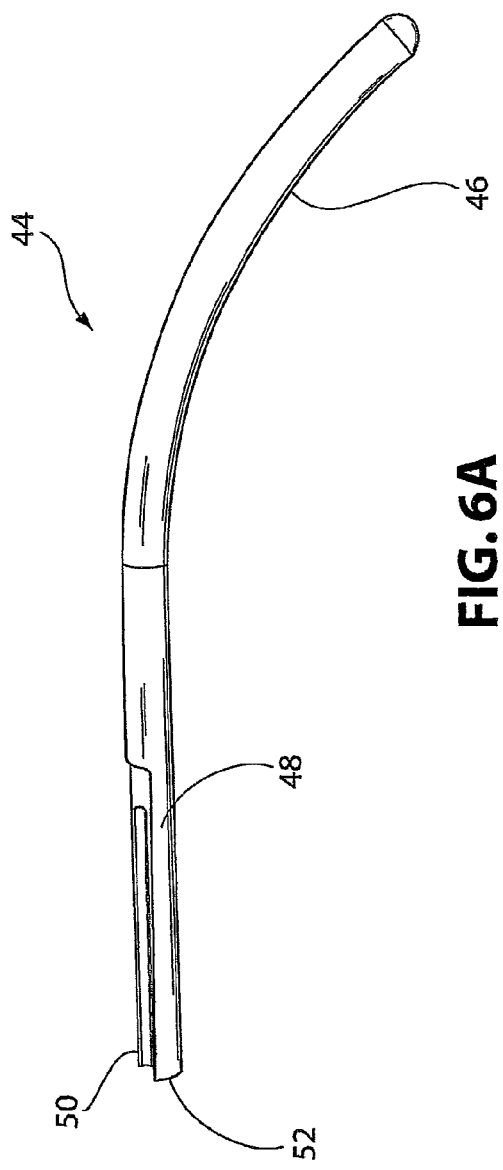
FIG. 6A is a side perspective view of an applicator made in accordance with the present invention.
Figure 6B:
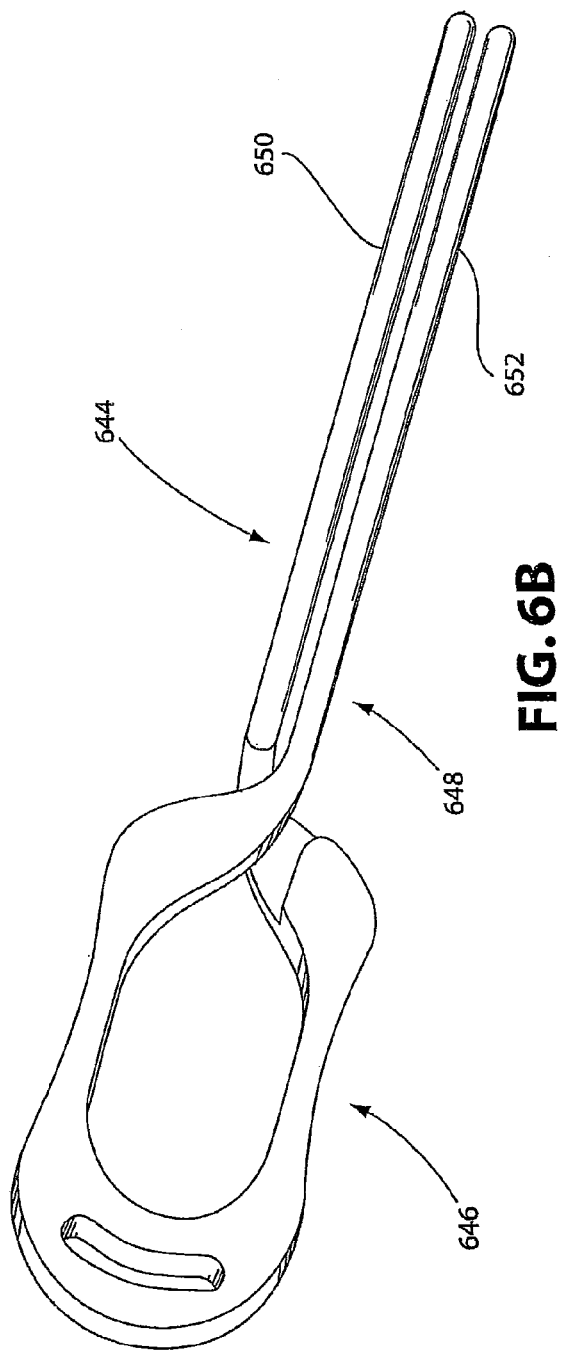
FIG. 6B is a side perspective view of an applicator that is made in accordance with the present invention.

With reference to FIGS. 6A, 6B and 7A, an applicator body 44 includes a holding region 46, a gripping mechanism 48 that may be comprised of forks or scissor-like arms, or other suitable mechanism 50, 52 for gripping and/or squeezing the nasal insert body or for conducting other relevant activities, such as applying an odorous material or medicine. The applicator 44 can be used to insert a nasal insert, or for various other applications such as, for example, removing the nasal insert, applying an odorous material or medicine, expanding the nasal insert, pumping liquid, air or other material, or positioning a nasal insert. The flexibility of the nasal insert body 8 in general, and along the second portion 12 in particular, can enable both manually compressing the nasal insert body 8, as well as compression with an applicator 44. In addition, a flexible region 54 may be defined on the nasal insert body 8 enabling collapsing through compression in a determined area and also providing higher comfort.

With reference to FIGS. 6A, 7A and 7B, the applicator 44 may be connected to the nasal insert body 8 by having the forks 50, 52 of applicator body 44 gripping the gripping area of the nasal insert body. When the forks 50, 52 are pressed further onto the flexible region 54 of nasal insert body 8, or to other relevant areas of nasal insert body 8, they create a squeezing action compressing the nasal insert body. Flexible region 54, or the other pressed part of nasal insert body 8, in turn applies frictional resistance against the forks 50, 52, thereby retaining the applicator 44 until it is manually removed. Alternatively, FIG. 6B shows an applicator body 644 having scissor arms 650, 652 that can grip the gripping portion of the nasal insert body 8, or other part, and hold the nasal insert body squeezed using the flexibility and compressibility of the nasal insert shape and materials. The applicator, in general, may further include a stopper (not shown) for preventing insertion of the insert too deep into the nose for safety purposes. In addition, a stopper may also be added to stop the fork/scissor-like arms or other relevant part of an applicator from sliding off of the gripping portion of the nasal inset body 8 when they are connected. The applicator shape and the correlated method of gripping and compressing are not meant to be limiting, as other methods and shapes may be applied. In addition the applicator may further allow reduced rigidity along the nasal insert body 8 in general, and along the air passageway 26 and the second portion 12 in particular, as the applicator will prevent the nasal insert from folding through insertion. Gripping portion, such as 58, and/or flexible area, such as 54, can also be applied to the first portion 10 of the nasal insert body 8, allowing smooth comfortable insertion of the head 14 as well. The use or presence of an applicator is not meant to be limiting as many embodiments that do not use any applicator can serve as well. Also, the presence of a dedicated flexible area is optional as the nasal insert body can flex without it. For example, the nasal inserts shown in FIGS. 2A and 2B have a gripping portion 58, but do not have the flexible area 54. FIG. 7B shows a compressed nasal insert body 8 with an applicator body 44 connected.

Alternatively, the fork/scissor-like arms, or other relevant mechanism, may grip the gripping portion of the nasal insert body 8 and hold the nasal insert body squeezed using the flexibility and compressibility of the nasal insert shape and materials or by causing a collapsing in a different designated flexible area along the nasal insert body 8. A gripping region 58 of the nasal insert body 8 may further act as a guide for insertion. The shape of the gripping portion 58 is not meant to be limiting, as other shapes can be applied for the same purpose, for example, the gripping portion as shown in FIGS. 2A and 2B. When the applicator 44 is connected to the nasal insert 2, the forks 50, 52 may hold the nasal insert in a squeezed position. The use of fork or scissor-like arms or another relevant mechanism for gripping the nasal insert body 8, or for squeezing and expanding it, or for any other use of the applicator is not meant to be limiting as many other mechanisms may perform these functions. The nasal insert body 8 may further include a gripping area. With reference to FIG. 7A, the gripping area 58 will be held by an applicator 44. The applicator 44 may also squeeze the nasal insert body 8, allowing the nasal insert body 8 to pass easily into the nasal cavity 100. The forks 50, 52 are retained on the gripping area of the nasal insert body 8 by a combination of restive pressure and the whole gripping region 58, and will remain in place until the user pulls the applicator 44 out from the nasal insert 2. The applicator shape and the correlated method of gripping and compressing are not meant to be limiting, as other methods and shapes may be applied.

The applicator 44 can navigate the nasal insert 2 into the nasal cavity 100 and can also be used to adjust the nasal insert 2 inside the nasal cavity 100. In addition, the applicator 44 can compress and open the nasal insert 2 when inserting and also removing the nasal insert 2. Nasal inserts can be offered with or without an applicator. Applicator 44 can be made of a rigid and sturdy but yet elastic material such as plastic, metal and rigid silicon. The applicator 44 can be more rigid than the nasal insert 2, thereby allowing the nasal insert 2 to be navigated by the applicator 44. The type of material is non-limiting, as other materials can be used to make the applicator 44.

Additional embodiments are shown in FIGS. 8A, 8B, 9, 10 and 11. FIG. 8A shows an embodiment of a nasal insert 202 having an enlarged rounded rectangular shaped head 214 in a first portion 210 and an L-shaped tail 216 in a second portion 212. The enlarged rounded rectangular shaped head 214 is surrounded with a bulge 220 that can be used as a grip for another layer, or as a sealing member, or as a groove for a spring and can also provide flexibility inside the nasal cavity 100 to expand into the nasal cavity 100, forming a tight seal within. An optional layer 218 can be made of absorbent or non-absorbent material providing better sealing and higher comfort and can fully or partially cover the walls of the head 214. With reference to FIG. 8B, the tail 216 of nasal insert 202 can be formed of an "L" shape and forms an L-shaped air passageway 226 therethrough. The "L" shape suits the internal natural nasal cavity shape.

Figure 9:
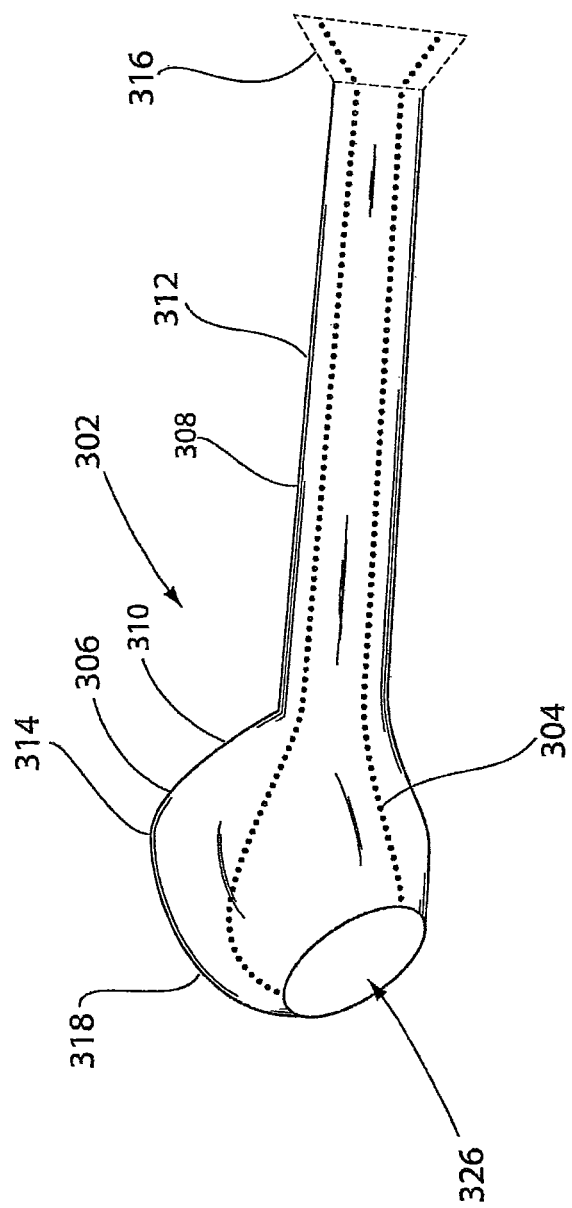
FIG. 9 is a side view of a nasal insert having a bulbous head and a flared second end shown in phantom made in accordance with the present invention.

FIG. 9 shows a flexible nasal insert 302 having a wider bulbous round head 314 in a first portion 310 and a thinner second portion 312. The air passageway 326 has a wider air passageway in the first portion 310 and it narrows through the second portion 312. The outer soft surface can be made of absorbent or non-absorbent compressible or non-compressible material, and the inner surface more rigid but elastic. Also, the inner layer can be made of sealed material preventing odor particles from moving through it, thereby compelling the user to breathe through the mouth. The air passageway 326 enables easier movement of air through the nasal insert 302. The nasal insert 302 can be positioned in the nasal cavity and the head 314 will form a snug fit with nasal vestibule 105 internal walls and block the air from flowing around the head directing it into the air passageway 326. The air passageway 326 may bypass the olfactory area or direct the air to bypass the olfactory area.

Alternatively, the surface 318, or the entire outer surface 306, of the nasal insert 302 can be made of a high density sealing material or an additional layer of high density sealing material can be placed on a first layer of spongy or porous material or the outer surface covering it fully or partially. The high density material can prevent any inhaled or exhaled air from reaching the olfactory region 350 of the nasal cavity 300 and contributes good drainage of the mucus.

Alternatively, air passageway 326 can be fully or partially filled with material, or the whole device can be made of porous material. In this case, the nasal insert body 308 can be fully or partially covered with a sealing layer.

With continuing reference to FIG. 9, the length of the nasal insert 302 can be varied by increasing and decreasing the length of the second portion 312. The nasal insert 302 can also include a tail 316 (shown in phantom). Tail 316 directs the exhaled air to move out more easily through the nasal insert body and directs it into the air passageway and by that assists in preventing it from the olfactory region 150. It also supports the formation of an air lock in a sturdier manner and contributes to preventing or significantly reducing the amount of odor reaching the olfactory area.

Figure 10:
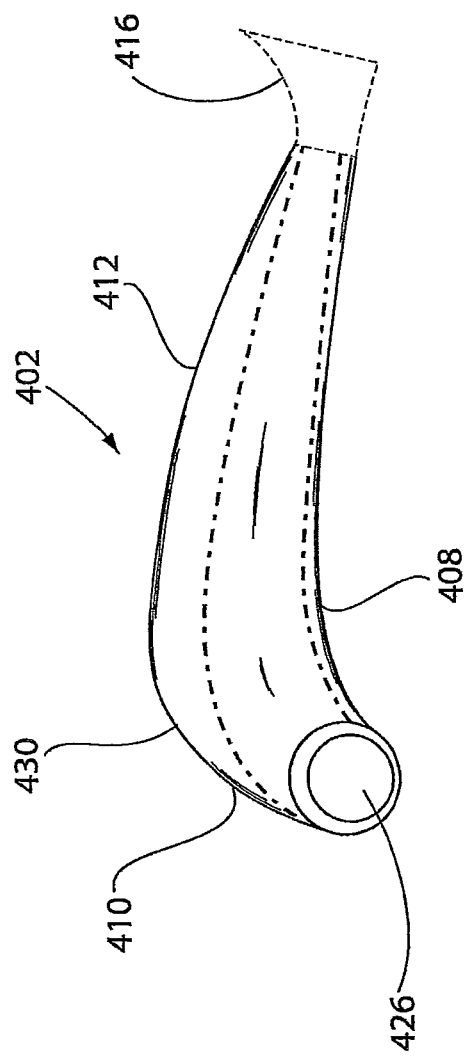
FIG. 10 is a side view of another design of a nasal insert made in accordance with the present invention.

FIG. 10 shows a nasal insert 402 having an alternative convex shape. Nasal insert 402 having a first portion 410 includes a curved body 408 and curved air passageway 426 therethrough. The curve of nasal insert body 408 can fit nasal cavity 100. The region between the first portion 410 and second portion 412 can use layered material to form a sealing member 430 that can press against the nasal cavity 100 forming a tight seal. A tail 416 (shown in phantom) can be included having a wider air passageway in the second portion 412 to aid respiration and direct exhaled air into the air passageway more easily, and to better form the air lock that assists in preventing odor from reaching the olfactory area.

Figure 11:
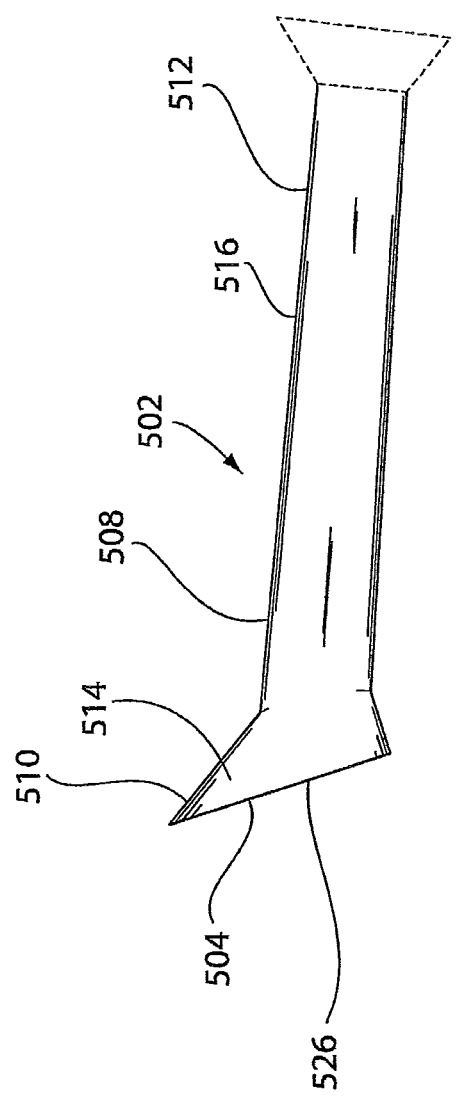
FIG. 11 is a side view showing a nasal insert having a flared head made in accordance with the present invention.

FIG. 11 shows a nasal insert 502 having a first portion 510 and a second portion 512 having a flared head 514 and a tail 516. The inner surface 504 defines an air passageway 526 through the nasal insert 502. The air passageway 526 can remain constant, decrease or increase in width or can change in shape. The tail 516 can decrease in width or remain constant, or increase from the first portion 510 to the second portion 512. The length of the tail can vary and the shape of it as well, such as flared tail, non-flared tail, oblique general length, and the like.

The present invention also provides a method for reducing or eliminating the urge to smoke and smoking in general by suppressing the body's physiological desire to smoke in many aspects, for example: the desire to smoke instigated by perceiving smells in general or by specific smells which are connected to the user's habits associated with smoking. For example, many smokers may be urged to smoke after smelling coffee, food, other peoples' smoke or other smells. It may also suppress the physical desire to smoke by causing the user to have a reaction of sickness and/or disgust while trying to smoke or while being in a smoking environment or even cause repulsion from thinking about smoking. This physical reaction leads to the outcome that the invention is also enabling smokers to smoothly overcome, with very little struggling, the challenging period of defeating the physical addiction to nicotine, when the body is cleaning itself from the nicotine. The present invention also flattens the smoking experience and makes smoking flavorless. In addition, the present invention suppresses smoking and the urge to smoke by causing the user to feel disgust and sickness while trying to smoke, as if he/she had been ill. While using the invention, the user might feel like he/she is experiencing some symptoms of a mild cold and slight runny nose without actually being ill or without experiencing other illness symptoms such as fever. In addition, the invention may create additional discomfort when used by smokers who are used to exhaling the smoke through their nose, as exhalation may be slower than usual or blocked.

The invention may also support smokers' efforts to avoid gaining weight while quitting smoking, as it flattens the eating experience and reduces impulse eating and causes the user to eat less and less often. In addition, this invention may cause a flat and less enjoyable smoking experience due to weakening smelling. First, a nasal insert 2, as shown in FIG. 2A, is provided having an air passageway 26. The nasal insert 2 is inserted into the nostril 110 and into the nasal cavity 100. The nasal insert 2 can be inserted, as previously described hereinabove, by pressing the nasal insert body 8 between two fingers of the hand, or by using an applicator, or in any other suitable manner, or it can be compressed in the first place. The user can lift the hand with the nasal insert 2 up toward the nose and under the nostril 110. The user then pushes the nasal insert body 8 into the nasal cavity, and one nasal insert can be inserted through each of the right and left nostrils and directed into the nostril 110 with the user's fingers or by using an applicator. Using the fingers or an applicator 44, as shown, for example, in FIG. 2B, the adjustment of the nasal insert 2 can be made. The user can position the nasal insert body 8 to fit snuggly inside the nasal cavity 100. In alternative embodiments, a premolded liquid or body temperature activated insert or an insert premolded with an applicator, can be provided, which can be inserted into the nose and pushed inside the nasal cavity. Once inside, the mucus and bodily fluids or external dropping of liquid or body temperature or other relevant act, such as, for example, manually turning or opening the applicator can activate the premolded nasal insert 2 to decompress inside the nasal cavity 100 and expand into the nasal cavity 100 forming a tight but comfortable fit. The premolded nasal insert 2 can also be activated using an applicator 44 having liquid thereon which can be placed on the nasal insert body 8, or by applying some other act to the nasal insert. A nasal insert that does not require the above process, is applicable as well. For example, a nasal insert, which shape is fixed, can simply be pushed into the nasal cavity to the right position, adapting its flexible body to the nasal internal anatomy (or being suitable at the first place) without the need of changing shape due to body temperature, liquid etc. Once inside the nasal cavity 100, the head 14 of the nasal insert 2 can stretch and form a comfortable fit and also block inhaled air from passing around the nasal insert 2 and thereby directing the inhaled air to pass in through the air passageway 26. Sealing members 30, 32, 34, 36 and 38 of FIGS. 2A and 2B, or others, can also aid in forming a seal and blocking air, thereby directing the air through the nasal insert air passageway and/or forming an air lock in nasal cavity 100. When the user begins breathing after inserting the nasal insert body 8, the inhaled air is directed into the air passageway 26 and through the nasal insert body 8 to the respiratory passages of the user. Exhaled air is also directed into the air passageway 26 and out through the head 14 of the nasal insert body 8. This direction of air creates a bypass of olfactory region 150 and in doing so, prevents or significantly reduces or delays odors from reaching the olfactory region 150. By preventing the odors from reaching the olfactory region 150, any odor that is related to smoking is also inhibited. Taste and smell are physiologically interdependent and distinct flavors are produced by aromas stimulating olfactory chemo-receptors in the olfactory area. Basic taste is perceived by gustatory papillae in the oral cavity and throat, but this sensation is limited to sweet, bitter, sour and salty. More complex flavors such as cigarette ones are elaborated by smelling odorous particles coming in contact with the olfactory area. Therefore, this invention flattens the smoking experience and makes it less flavorful and less enjoyable by reducing or eliminating one's sense of smell. In addition, smelling receptors are connected directly to the cortex and different smells may lead to the creation of an instinct and sometimes uncontrolled desire to smoke, which leads to impulsive smoking. By eliminating or reducing one's sense of smell, this invention assists the user to avoid or significantly reduce impulse smoking. Often, smokers are urged to smoke simply by associating a particular smell, such as the smell of coffee, food or second-hand smoke from other smokers, with the activity of smoking. By suppressing other smells from reaching the olfactory region 150, the present invention additionally reduces impulse smoking caused by sensing other smells. Because the perception of odors in the user's vicinity is substantially reduced, the user is unable to associate those smells with smoking, and is thereby less likely to have a desire to smoke. The reduction of smell also results in a flat flavorless, and generally less enjoyable, smoking experience once the user smokes, and, therefore, cause the user to be less inclined to smoke or to smoke less in general. Even when the user has already started smoking, he/she may not finish the cigarette or the other smoking substance due to the use of the invention, and will reduce or quit smoking as well.

Furthermore, the reduction in smoking and the desire to smoke is additionally achieved through the increased secretion of mucus in the nasal cavity or from the creation of the symptoms similar to a mild cold. The desire to smoke can also arise from seeing or smelling other people smoke or associating smoking with a particular activity. For example, a smoker may have an urge to smoke when socializing with other smokers, driving a car, talking on the telephone or any other habitual activity. The increased secretion of mucus in the nasal cavity, as well as the partial blockage of the nasal cavity, make smoking uncomfortable and even repulsive for the user, and, therefore, causes the user to reduce or totally quit smoking. This phenomenon also reduces or even eliminates the user's desire and urge to smoke in general. Continuous daily use of the nasal insert 2 leads to the elimination of the urge to smoke triggered by associating smoking with a particular activity, and enables the user to have a period of time to establish a new routine, or even the same routine that will not be associated with smoking. The use of the nasal insert in the first and most difficult period of smoking cessation efforts will assist the user in going through this period much more easily and to establish a way of life without smoking.

One of the most difficult barriers to overcome while attempting to quit smoking is the addiction to nicotine. While the present invention does not directly eliminate the user's dependence on nicotine, it can be helpful in assisting the smoking cessation process in this aspect as well. Generally, the presence of nicotine in the smoker's blood system is eliminated after several days of not smoking. This period and the few weeks after it are often the most difficult for most smokers attempting to quit smoking because of the sudden withdrawal of the drug from the blood system. Many smokers who have been unsuccessful in quitting smoking attribute their inability to quit to this initial period. The nasal insert 2 also assists in the aspect of recovering from the addiction to nicotine in the smoking cessation process by making smoking uncomfortable and sickening. This repulsion to smoking and the smoking cessation caused by it leads to the elimination of nicotine from the blood system without the necessity to depend on will power or to struggle against the physiological need for nicotine. Such transition is not particularly difficult for the smoker because he/she does not experience the urge to smoke due to the repulsive reaction to it caused by the present invention. Furthermore, the present invention may be used in conjunction with other known smoking cessation aids, such as nicotine patches, nicotine gums, and other means. When continuously used according to instructions for several weeks, or for a different period of time, and according to the relevant instructions, which is suitable for this purpose, the nasal insert 2 contributes to the total elimination of nicotine from the user's blood system, and to acclimation of the user's body to living without the need for nicotine. The nasal insert 2 thereby smoothly and completely eliminates the user's dependence on the drug. The present invention may further comprise written instructions describing how the nasal insert 2 is to be used. The instructions may comprise information on how the nasal insert 2 is to be used in overcoming nicotine addiction caused by smoking.

To remove the nasal insert 2, the user can push air out sharply while wiping the nose, by sneezing very strongly, or snorting outward through the nasal cavity 100, causing the nasal insert 2 to fall forward through a nostril 110 from where it can be pulled completely out of a nasal cavity 100. It can also be removed by pushing it out through the nose by gently squeezing the lower part of the nose from outside or by inserting a finger into the nasal vestibule and pulling it out. Further, the nasal insert 2 can be pulled out using the applicator 44. Still further, threads can be attached to the nasal insert body 8 for pulling the nasal insert 2 out of the nasal cavity 100. The method of removal is not meant to be limiting, as many methods will work. Alternative inserts of varying shapes and sizes, as described hereinabove, can be removed in a similar method.

Once the nasal insert body 8 has been used, the user can either clean the nasal insert body 8 and use it again, or can dispose of the nasal insert body 8, depending on the specific material and embodiment, and of other parameters, such as medical instructions of use. One indication that the nasal insert body 8 should be replaced is mucosal saturation on the nasal insert body 8 in case of absorbent material. The nasal insert can be used continuously for a period of time, subject to the relevant limitations, such as materials, medical, supporting smoking cessation instructions and others. Instructions can be provided defining a period of time that the nasal insert body 8 can be used, for example, a period of several hours before removing to allow the nasal mucosa to rest, or for other reasons. It may also include recommendations and instructions regarding using one or two nasal inserts each time, depending on the desired effect or on other considerations. Alternatively, the nasal insert body 8 can be used only when the user is close to smoking-related odors or when the user is going to be in a situation that may lead him/her to smoke and he/she would like to avoid smoking or while the user is sleeping, when the user wishes to avoid or reduce snoring or obstructive sleep apnea, or it can be used while concentrating and studying for a test, etc. The specific occasion and method of use is dependant upon the desired effect, as well as of medical and material parameters, and on other relevant considerations. The nasal insert body 8 can be made in a long lasting format which is reusable, or, alternatively, it can be made in disposable format allowing one or only a few uses before disposing. In an alternative disposable model, biodegradable materials can be used to make the nasal insert body 8. When re-using the same nasal insert body 8, it is recommended that it is cleaned before the re-use.

When the nasal insert body 8 is inserted inside the nostril 110, the nasal insert 2 can be worn without or almost without visual detection from the outside of the nose. Alternatively, the nasal insert 2 can include decorative elements or attachments, such as nose rings and jewelry (not shown), or the nasal insert 2 can be colored and extend beyond the nostril up to the outer side of the nose and/or down towards the mouth or towards the septum and the middle of the nose or other. The direction or specific shape or method are not meant to be limiting as many alternatives may serve. In yet a further embodiment of the present invention, the nasal insert 2 can be a nasal cover and be worn outside the nasal cavity. In this embodiment, the nasal insert 2 is preferably secured to the exterior of the nose and it either partially or fully blocks the passage of air into the nasal cavity. In an embodiment where the air passageway is at least partially obstructed, respiration through the nose will take place at a much reduced rate. As a result, smokers who are inclined to exhale the smoke through the nose while smoking will experience discomfort in maintaining this practice. This discomfort associated with smoking further aids in helping the smoker suppress or eliminate the urge to smoke and to less enjoy smoking in general. The user may apply the nasal insert externally on the nose by a friction fit or adhesive means, or by tying it to the ears or by many other methods. The specific method is not meant to be limiting as many methods may be applied.

As described before, in addition to all the above, the nasal insert 2 of this invention can be used for reducing and preventing snoring. The nasal area of the respiratory mucosa is particularly sensitive to changes in the blood flow and when congested, it produces a partial or total blockage in the air passages. When a person is in a supine position, for example, when sleeping, the nasal congestion usually produces a partial blockage of the nasal airway. To overcome this blockage, an increase of negative pressure is required to maintain nasal respiration. The increase of negative pressure in the nose, together with muscle relaxation at sleep, will produce vibrations of the soft palate, which is the most common mechanism that causes snoring. By introducing the device into the nasal air passages, an open airway is achieved at the nasal level. Therefore, used during sleep, the device will reduce or eliminate the snoring produced when sleeping in a supine position by maintaining open air passages at the nasal level. In this case, the method of use would be wearing the device in one nasal cavity, or in both nasal cavities, just before sleeping in order to have it while sleeping and taking it out upon waking. In many cases, the use in one nasal cavity will be enough, but in order to achieve a stronger impact, the use in both nasal cavities would be preferred.

In addition, the nasal insert 2 of this invention may be used for reducing and/or preventing obstructive sleep apnea. The same mechanism which increases negative pressure in order to maintain respiration when lying down is responsible for the obstructive sleep apnea in most people suffering from this symptom. The obstructive sleep apnea is caused by collapse of the pharyngeal walls into the airway. This is produced by the combination of increased negative pressure in the air passages during respiration, while the person is in a supine position, and the relaxation of the pharyngeal muscles during sleep. The collapse of the pharyngeal walls will produce a partial or total blockage of air passages at the level of the oropharynx. By maintaining an open nasal passage, the nasal insert reduces the negative respiratory pressure, which eliminates the main cause of air passage collapse at the pharyngeal level. Hence, the nasal insert will reduce the severity or eliminate obstructive sleep apnea. Also, the present invention is a method of use of the nasal insert 2 which can be inserted into one nasal cavity, or in both nasal cavities, just before sleeping in order to have it while sleeping and then taking the nasal insert out upon waking. In many cases, the use of the nasal insert 2 in one nasal cavity will be enough, but in order to achieve stronger impact, the use of nasal inserts 2 in both nasal cavities would be preferred.

In addition to the above-described effects, the present invention also may have the effect of enlarging the nasal natural air passageway. The nasal valve is the narrowest air passageway of the upper respiratory system and it generates a large part of the overall natural nasal resistance to air flow. The nasal insert of this invention, in the relevant measure for such application, may force a larger cross section for air flow in the nasal valve area and contribute to easier breath in general as well as to reduction or elimination of snoring or of obstructive sleep apnea. In other words, the nasal insert passageway 26 cross-sectional area or effective diameter over the complete passageway length is larger than the cross-sectional area or effective diameter of the nasal valve when the nasal insert 2 is not placed within the nasal cavity. It may also assist athletes, students or any other person who needs increased air consumption and oxygen for a specific need or in general.

It will be readily appreciated by those skilled in the art that modifications may be made to the invention without departing from the concepts disclosed in the foregoing description. Accordingly, the particular embodiments described in detail herein are illustrative only and are not limiting to the scope of the invention, which is to be given the full breadth of the appended claims and any and all equivalents thereof.

The claimed invention is:

1. A method for reducing or suppressing a smoker's desire to smoke and a method for reducing or quitting smoking of smoking substances, comprising the steps of:
    providing a nasal insert, said nasal insert including a body for insertion into a nasal cavity, said nasal insert body comprising an inner surface defining an air passageway, and an outer surface having a first portion and a second portion, said outer surface configured to form a seal between said nasal insert body and the nasal cavity;
    inserting said nasal insert body into the nasal cavity such that the nasal insert body rests against a portion of the nasal cavity
    creating a sealing between said nasal insert body and the nasal cavity; and
    wherein the nasal insert body creates a bypass of the olfactory region or directs the air to bypass the olfactory region thereby delaying, blocking or reducing the amount of odors reaching the olfactory region.

2. The method of claim 1, wherein insertion of the nasal insert body into the nasal cavity causes an increase in mucus secretion in the nasal passage to block, prevent, reduce, or delay smelling.

3. The method of claim 1, wherein insertion of the nasal insert body into the nasal cavity causes an increase in mucus secretion in the nasal passage to contribute to the sensation of a light runny nose or a mild cold.

4. The method of claim 1, wherein use of the nasal insert contributes to and/or creates a feeling of sickness or disgust while attempting to smoke; thereby reducing or eliminating the craving to smoke, and/or reducing or eliminating smoking.

5. The method of claim 1, further comprising the step of inserting the nasal insert body into the nasal cavity such that it fully or partially blocks the nasal cavity, creating a sensation of a light runny nose or a mild cold.

6. The method of claim 1, wherein the nasal insert body is compressed prior to insertion into the nasal cavity and then the nasal insert body expands after insertion in the nasal cavity.

7. The method of claim 1, wherein the nasal insert body forms an air lock in the nasal cavity.

8. The method of claim 1, wherein said nasal insert is inserted, compressed, expanded, or removed by an applicator.

9. The method of claim 1, wherein use of the nasal insert flattens the smoking experience making it less flavorful and/or enjoyable.

10. The method of claim 1, wherein use of the nasal insert reduces or eliminates the urge to smoke instigated by smell.

11. The method of claim 1, wherein use of the nasal insert slows or prevents smoke exhalation through the nose, thereby creating a less comfortable or less enjoyable smoking experience.

12. The method of claim 1, further comprising the step of using the nasal insert body at least until overcoming nicotine addiction caused by smoking.

13. The method of claim 1, further comprising the step of using the nasal insert body at least until overcoming the urge to smoke caused by smoking related habits.

14. The method of claim 1, wherein said nasal insert is used for an amount of time wherein the smoker's desire to smoke has been reduced, a smoking habit has been broken, and/or until a smokeless routine has been established.

15. The method of claim 1, further comprising the step of placing the nasal insert body inside the nose such that it is undetectable or almost undetectable when viewed from outside the nose.

16. The method of claim 1, wherein said nasal insert body is worn continuously for a period of time.

17. The method of claim 1, wherein said nasal insert body is worn while smoking and /or while being in an environment that encourages smoking.

18. The method of claim 1, wherein the nasal insert body contains or comprises medicine.

19. The method of claim 1, wherein the nasal insert body is inserted only inside one nasal cavity.

20. The method of claim 1, wherein the nasal insert body is inserted into both nasal cavities.

21. The method of claim 1, wherein said nasal insert is worn continuously for a period of time, then removed for a period of time, and worn again and so on until smoking is significantly reduced or totally eliminated.

22. The method of claim 1, wherein the nasal insert body extends into and beyond the nasal valve.

23. The method of claim 1, wherein said nasal insert body is configured to be fully located in the nasal cavity.

24. A method for reducing or suppressing a smoker's desire to smoke and a method for reducing or quitting smoking of smoking substances comprising the steps of:
providing a nasal insert, said nasal insert including a nasal insert body for insertion into a nasal cavity, said nasal insert body comprising an inner surface or material, and an outer surface or material having a first portion and a second portion, said nasal insert body being adapted to fit inside a nasal cavity;
inserting said nasal insert body into the nasal cavity such that the nasal insert body rests against a portion of the nasal cavity, creating at least a partial blockage of the nasal cavity; and
wearing the nasal insert body for an amount of time wherein wearing of the nasal insert body creates a feeling of a mild cold and/or light runny nose, and/or a feeling of sickness or a feeling of disgust and/or less enjoyable or less comfortable experience while attempting to smoke, resulting in a reduction or elimination of the user's craving to smoke and/or in reduction or elimination of the amount of smoking of smoking substances.

25. The method of claim 24, wherein the nasal insert is used for an amount of time wherein the smoker's desire to smoke has been reduced or a smoking habit has been broken and/or until a smokeless routine has been established.

26. The method of claim 24, wherein the nasal insert body forms an air lock in the nasal cavity.

27. The method of claim 24, further comprising the step of placing the nasal insert body inside the nasal cavity such that it is undetectable or almost undetectable when viewed from outside the nose.

28. The method of claim 24, wherein said nasal insert is worn continuously for a period of time.

29. The method of claim 24, wherein said nasal insert is worn continuously for a period of time, then removed for a period of time, and worn again and so on until smoking is significantly reduced or totally eliminated.

30. The method of claim 24, wherein said nasal insert is worn while smoking and/or while being in an environment that encourages smoking.

31. The method of claim 24, wherein use of the nasal insert prevents odors from reaching the olfactory region or reduces the amount of odors reaching the olfactory region or delays an amount of time for odors to reach the olfactory region, thereby flattening the smoking experience and making it less flavorful or enjoyable and thereby reducing the user's craving to smoke and/or reducing the amount of smoking of smoking substances.

32. The method of claim 24, wherein the nasal insert body contains or comprises medicine.

33. The method of claim 24, wherein use of the nasal insert reduces the user's urge to smoke wherein the urge is instigated by smell.

34. The method of claim 24, wherein use of the nasal insert slows or prevents smoke exhalation through the nose creating a less comfortable or less enjoyable smoking experience.

35. The method of claim 24, further comprising the step of using the nasal insert body at least until overcoming nicotine addiction caused by smoking.

36. The method of claim 24, wherein use of the nasal insert flattens the smoking experience and makes it less flavorful and/or enjoyable.

37. The method of claim 24, wherein the nasal insert body is compressed prior to insertion into the nasal cavity and the nasal insert body expands after insertion in the nasal cavity.

38. The method of claim 24, further comprising the step of using the nasal insert body at least until overcoming the urge to smoke caused by smoking related habits.

39. The method of claim 24, wherein the nasal insert body is inserted inside only one nasal cavity.

40. The method of claim 24, wherein the nasal insert body is configured to be fully located inside the nasal cavity.

41. The method of claim 24, wherein the step of inserting the nasal insert body into the nasal cavity includes the use of an applicator having a gripping mechanism configured for gripping and squeezing the nasal insert body and assisting in navigating the nasal insert body during insertion, said gripping mechanism configured to prevent folding of the nasal insert body during insertion.

* * * * *

UNITED STATES PATENT AND TRADEMARK OFFICE
CERTIFICATE OF CORRECTION

PATENT NO. : 8,839,790 B2  Page 1 of 1
APPLICATION NO. : 12/841511
DATED : September 23, 2014
INVENTOR(S) : Adva Beck Arnon It is certified that error appears in the above-identified patent and that said Letters Patent is hereby corrected as shown below:

In The Claims

Column 21, Line 60, Claim 24, delete "while" and insert -- in which when --

Column 21, Line 61, Claim 24, delete "resulting" and insert -- results --

Signed and Sealed this
Twenty-seventh Day of January, 2015

Michelle K. Lee
*Deputy Director of the United States Patent and Trademark Office*